US011582956B2

(12) United States Patent
Zhu et al.

(10) Patent No.: US 11,582,956 B2
(45) Date of Patent: Feb. 21, 2023

(54) RECOMBINANT ADENOVIRUS-BASED INTERFERON BIOTHERAPEUTICS IN SWINE

(71) Applicant: The United States of America, as Represented by the Secretary of Agriculture, Washington, DC (US)

(72) Inventors: James J. Zhu, Niantic, CT (US); Elizabeth A. Bishop, Shelter Island, NY (US); Palaniappan Ramanathan, Dickinson, TX (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 485 days.

(21) Appl. No.: 16/558,501

(22) Filed: Sep. 3, 2019

(65) Prior Publication Data
US 2020/0100479 A1 Apr. 2, 2020

Related U.S. Application Data

(60) Provisional application No. 62/737,438, filed on Sep. 27, 2018.

(51) Int. Cl.
| | |
|---|---|
| *A01N 63/00* | (2020.01) |
| *A01K 67/027* | (2006.01) |
| *C12N 15/86* | (2006.01) |
| *C12N 15/90* | (2006.01) |
| *C07K 14/52* | (2006.01) |
| *C12N 15/85* | (2006.01) |

(52) U.S. Cl.
CPC .......... *A01K 67/0275* (2013.01); *C07K 14/52* (2013.01); *C12N 15/86* (2013.01); *C12N 15/907* (2013.01); *A01K 2207/15* (2013.01); *A01K 2217/056* (2013.01); *A01K 2217/072* (2013.01); *A01K 2217/15* (2013.01); *A01K 2217/206* (2013.01); *A01K 2227/108* (2013.01); *A01K 2267/01* (2013.01); *C12N 2015/8518* (2013.01)

(58) Field of Classification Search
None
See application file for complete search history.

(56) References Cited

U.S. PATENT DOCUMENTS

2004/0072752 A1  4/2004  Nash et al.

FOREIGN PATENT DOCUMENTS

WO  2007081336 A1  7/2007

OTHER PUBLICATIONS

Chinsangaram, J. Virol., 77: 1621-1625 (2003).*
Dias, Journal of Interferon & Cytokine Research, 31: 227-236 (2011).*
Moraes, Vaccine, 22: 268-279 (2003).*
Logan (PNAS, 1984, vol. 81, p. 3655-3659).*
International Search Report, dated Jan. 3, 2020.
Zhu, James J., Improvement of Interferon Biotherapeutics for Foot-and-mouth Disease in Swine-NPB #14-014, Research Report Swine Health, May 26, 2017, pp. 1-23, Pork Checkoff—National Pork Board, Des Moines, Iowa.
Du, Yijun, Immune responses of recombinant adenovirus co-expressing VP1 of foot-and-mouth disease virus and porcine interferon α in mice and guinea pigs, Science Direct—Veterinary Immunology and Immunopathology, Aug. 15, 2008, vol. 124, Issues 3-4, pp. 274-283.

* cited by examiner

*Primary Examiner* — Michael C Wilson
(74) *Attorney, Agent, or Firm* — John D. Fado; Mark D. McNemar

(57) ABSTRACT

Disclosed herein is a recombinant adenovirus genome, said adenovirus genome comprising a heterologous nucleic acid inserted into a cloning site of said genome, said heterologous nucleic acid comprising: (a) a first nucleic acid sequence comprising an adenovirus tripartite sequence (e.g., SEQ ID NO:1) operably linked to a second nucleic acid sequence encoding an interferon (e.g., SEQ ID NO:2); (b) a third nucleic acid sequence comprising a bovine growth hormone polyA termination sequence operably linked to said second nucleic acid sequence (e.g., SEQ ID NO:3); (c) a fourth nucleic acid sequence comprising a porcine elongation factor 1-alpha (EF1α) promoter (e.g., SEQ ID NO:4); (d) a fifth nucleic acid sequence operably linked to said fourth nucleic acid sequence, said fifth nucleic acid sequence encoding a suppressor of cytokine signaling 1 (SOCS1) protein (e.g., SEQ ID NO:5). Furthermore, there is disclosed a method of producing interferon in an animal (e.g., swine).

19 Claims, 26 Drawing Sheets

Specification includes a Sequence Listing.

FIG. 10

SEQUENCE LISTING

<160> NUMBER OF SEQ ID NOS: 6

<210> SEQ ID NO 1
<211> LENGTH: 201
<212> TYPE: DNA
<213> ORGANISM: Artificial Sequence
<220> FEATURE:
<223> OTHER INFORMATION: Synthetic

<400> SEQUENCE: 1

```
actctcttcg catcgctgtc tgcgagggcg agctgttggg ctcgcggttg aggacaaact      60
cttcgcggtc tttccagtac tcttggatcg gaaacccgtc ggcctccgaa cggtactccg     120
ccaccgaggg acctgagcgg tccgcatcga ccggatcgga aaacctctcg agaaaggcgt     180
ctaaccagtc acagtcgcaa g                                               201
```

<210> SEQ ID NO 2
<211> LENGTH: 570
<212> TYPE: DNA
<213> ORGANISM: Artificial Sequence
<220> FEATURE:

<223> OTHER INFORMATION: Synthetic

<400> SEQUENCE: 2

```
atggctccca cctccgcctt cctgaccgtg ctggtgctgc tgagctgcaa cgccatctgc      60
tgcctgggat gcgacctgcc acagacccac tccctggctc acaccagggc cctgagactg     120
ctggctcaga tgaggaggat ctccccttc agctgcctgg accacaggag agacttcggc      180
agcccacacg aggccttcgg cggaaaccag gtgcagaagg ctcaggctat ggccctggtg     240
cacgagatgc tgcagcagac cttccagctg ttctccaccg agggcagcgc cgccgcctgg     300
gacgagtccc tgctgcacca gttctgcacc ggcctggacc agcagctgcg cgacctggag     360
gcctgcgtga tgcaggaggc tggcctggag ggcacccac tgctggagga ggacagcatc      420
ctggccgtgc gcaagtactt caccggctg accctgtacc tgcaggagaa gtcctacagc      480
ccatgcgctt gggagatcat cagggctgaa gtgatgagag tgttcagctc cagccggaac     540
ctgcaggaca ggctgcggaa gaaggagtga                                      570
```

<210> SEQ ID NO 3
<211> LENGTH: 232
<212> TYPE: DNA
<213> ORGANISM: Artificial Sequence
<220> FEATURE:
<223> OTHER INFORMATION: Synthetic

<400> SEQUENCE: 3

```
gcggccgcct gtgccttcta gttgccagcc atctgttgtt tgcccctccc ccgtgccttc      60
cttgaccctg gaaggtgcca ctcccactgt cctttcctaa taaaatgagg aaattgcatc     120
gcattgtctg agtaggtgtc attctattct ggggggtggg gtggggcagg acagcaaggg     180
ggaggattgg gaagacaata gcaggcatgc tggggatgcg gtgggctcta tg             232
```

<210> SEQ ID NO 4
<211> LENGTH: 691
<212> TYPE: DNA
<213> ORGANISM: Artificial Sequence
<220> FEATURE:
<223> OTHER INFORMATION: Synthetic

<400> SEQUENCE: 4

```
gcggagagta attcatacaa aaggaggact ctcctcagcc agggaaatcc cagggaccgt      60
cgataaactc ccactaaacc tagaaccgag tgagcgctcg accccgcctc ccacccacca     120
gcagtcgtca tcctcctggt tgagaggagc atgcgccggg cgccgtgtgc tcgtcagtgg     180
gctgaacgca catcgcccac ggtccccgaa gatgggggga ggggacggcg gtggaaccgg     240
tgccgggtgg aggtggcgcg gggtaaactg gaaagtggt gtcgtgtgct ggctccgccc      300
ttttccccga gggtggggga ggaccatata taagcgccgt ggtccccgcg aacgttcttt     360
ttcgcaacgg gtttgccgcc aggacacagg tgagtacggg tgtggcctcc gtccgcatgg     420
cctccgccgg tggccacggc cttagcgtgc ctcccgcccc ccgcgcgta gagggctctg      480
cgccctggtc ctgattccga gctgcgggcg ggggaggtg gagaactcga ggccctccgc      540
tctcgcggtt ccctaccgcg tgccggtgg cggcctgctg gggcgccgtg gccgccgcgt       600
gcgatccgcg ccttcgcgcc cggtcgtcgg gacagtagta taaataaggt ttttgtcgtc     660
ttaggtgtcg tgaaagccat cgctaaaagc t                                    691
```

<210> SEQ ID NO 5
<211> LENGTH: 663

<212> TYPE: DNA
<213> ORGANISM: Artificial Sequence
<220> FEATURE:
<223> OTHER INFORMATION: Synthetic

<400> SEQUENCE: 5

```
atggtggctc acaaccaggt ggctgctgac aacgccatca gcaccgctgc tgagccacgc    60
cggaggcccg agcacagctc cagctccagc tccagctcca gctccagctc cagctccagc   120
tcccccggcg tgcccgcccg gcccaggccc tgcccagctg ccccgctcc agctccaggc    180
gacacccact tccggacctt caggagccac gccgactaca aaggatcac agggcctcc     240
gccctgctgg acgcttgcgg cttctactgg ggaccactgt ccgtgcacgg cgctcacgag   300
agactgaggg ctgagcccgt gggcaccttc ctggtgagag acagccggca gaggaactgc   360
ttcttcgctc tgtccgtgaa gatggccagc ggacccacct ccatcagagt gcacttccag   420
gctggccgct ccacctgga cggcagccgg gagtccttcg actgcctgtt cgagctgctg    480
gagcactacg tggctgctcc aaggaggatg ctgggagctc cactgagaca gagacgcgtg   540
cgccccctgc aggagctgtg cagacagagg atcgtggcta ccgtgggaag ggagaacctg   600
gctcgcatcc ccctgaaccc cgtgctgcgg gactacctga gctccttccc cttccagatt   660
tga                                                                  663
```

<210> SEQ ID NO 6
<211> LENGTH: 2388
<212> TYPE: DNA
<213> ORGANISM: Artificial Sequence
<220> FEATURE:
<223> OTHER INFORMATION: Synthetic

<400> SEQUENCE: 6

```
atcgatactc tcttcgcatc gctgtctgcg agggcgagct gttgggctcg cggttgagga    60
caaactcttc gcggtctttc cagtactctt ggatcggaaa cccgtcggcc tccgaacggt   120
actccgccac cgagggacct gagcggtccg catcgaccgg atcggaaaac ctctcgagaa   180
aggcgtctaa ccagtcacag tcgcaagcta gccaccatgg ctcccacctc cgccttcctg   240
accgtgctgg tgctgctgag ctgcaacgcc atctgctgcc tgggatgcga cctgccacag   300
acccactccc tggctcacac cagggccctg agactgctgg ctcagatgag gaggatctcc   360
cccttcagct gcctggacca caggagagac ttcggcagcc acacgaggc cttcggcgga    420
aaccaggtgc agaaggctca ggctatggcc ctggtgcacg agatgctgca gcagaccttc   480
cagctgttct ccaccgaggg cagcgccgcc gcctgggacg agtccctgct gcaccagttc   540
tgcaccggcc tggaccagca gctgcgcgac ctggaggcct gcgtgatgca ggaggctggc   600
ctggagggca ccccactgct ggaggaggac agcatcctgg ccgtgcgcaa gtacttccac   660
cggctgaccc tgtacctgca ggagaagtcc tacagcccat gcgcttggga gatcatcagg   720
gctgaagtga tgagagtgtt cagctccagc cggaacctgc aggacaggct gcggaagaag   780
gagtgagcgg ccgcctgtgc cttctagttg ccagccatct gttgtttgcc cctccccgt    840
gccttccttg accctggaag gtgccactcc cactgtcctt tcctaataaa atgaggaaat   900
tgcatcgcat tgtctgagta ggtgtcattc tattctgggg ggtggggtgg gcaggacag    960
caagggggag gattgggaag acaatagcag gcatgctggg gatgcggtgg gctctatggc  1020
ggagagtaat tcatacaaaa ggaggactct cctcagccag ggaaatccca gggaccgtcg  1080
ataaactccc actaaaccta gaaccgagtg agcgctcgac cccgcctccc acccaccagc  1140
```

```
agtcgtcatc ctcctggttg agaggagcat gcgccgggcg ccgtgtgctc gtcagtgggc    1200
tgaacgcaca tcgcccacgg tccccgaaga tgggggagg ggacggcggt ggaaccggtg    1260
ccgggtggag gtggcgcggg gtaaactggg aaagtggtgt cgtgtgctgg ctccgccctt    1320
ttccccgagg gtggggagg accatatata agcgccgtgg tccccgcgaa cgttctttt     1380 cgcaacgggt ttgccgccag gacacaggtg agtacgggtg tggcctccgt ccgcatggcc    1440
tccgccggtg gccacggcct tagcgtgcct cccggccccc cgcgcgtaga gggctctgcg    1500
ccctggtcct gattccgagc tgcgggcggg gggaggtgga gaactcgagg ccctccgctc    1560
tcgcggttcc ctaccgcgtg cccgtggcg gcctgctggg gcgccgtggc cgccgcgtgc    1620
gatccgcgcc ttcgcgcccg gtcgtcggga cagtagtata aataaggttt ttgtcgtctt    1680
aggtgtcgtg aaagccatcg ctaaaagctg ctagtcacca tggtggctca caaccaggtg    1740
gctgctgaca acgccatcag caccgctgct gagccacgcc ggaggcccga gcacagctcc    1800
agctccagct ccagctccag ctccagctcc agctccagct ccccggcgt gcccgcccgg    1860 cccaggccct gcccagctgc ccccgctcca gctccaggcg acacccactt ccggaccttc    1920
aggagccacg ccgactacag aaggatcacc agggcctccg ccctgctgga cgcttgcggc    1980
ttctactggg gaccactgtc cgtgcacggc gctcacgaga gactgagggc tgagcccgtg    2040
ggcaccttcc tggtgagaga cagccggcag aggaactgct tcttcgctct gtccgtgaag    2100
atggccagcg gacccacctc catcagagtg cacttccagg ctggccgctt ccacctggac    2160
ggcagccggg agtccttcga ctgcctgttc gagctgctgg agcactacgt ggctgctcca    2220
aggaggatgc tgggagctcc actgagacag agacgcgtgc gccccctgca ggagctgtgc    2280
agacagagga tcgtggctac cgtgggaagg gagaacctgg ctcgcatccc cctgaacccc    2340
gtgctgcggg actacctgag ctccttcccc ttccagattt gatctaga                2388
```

RECOMBINANT ADENOVIRUS-BASED INTERFERON BIOTHERAPEUTICS IN SWINE

REFERENCE TO RELATED APPLICATION

This application claims the benefit of U.S. Provisional Application No. 62/737,438, filed 27 Sep. 2018, which is incorporated herein by reference in its entirety.

GOVERNMENT LICENSE RIGHTS

This invention was made with funds provided by National Pork Board (Project #: 14-014) and government support under contract number HSHQDC-11-X-00189 awarded by U.S. Department of Homeland Security. The government has certain rights in the invention.

BACKGROUND OF THE INVENTION

Foot-and-mouth disease virus (FMDV) is a positive-sense, single-stranded RNA virus belonging to the *Aphthovirus* genus of the Picornaviridae family and causes an acute vesicular disease in cloven-hoofed animals including cattle, swine, goats, and sheep. It is one of the most contagious animal viruses and could have a devastating economic effect on livestock industries if outbreaks occurred, especially in FMD-free countries. There are commercial FMD vaccines available, however it takes approximately a week for the vaccine to induce protective immunity. Development of a countermeasure with a rapid onset of immunity would greatly facilitate the control of this disease.

FMDV has been known to be very sensitive to the inhibition of type I interferons (IFN) (Chinsangaram, J., et al., J. Virol., 73: 9891-9898 (1999); Sellers, R. F., Nature. 198, 1228-1229 (1963)). Because of their rapid and potent antiviral effects, type I IFN genes have been used to induce rapid onset of immune protection against FMDV in swine. Pigs can be completely protected against FMDV challenge 24 h after injection with a replication-defective human adenovirus 5 (Ad5) inserted with an IFNα gene (Chinsangaram, J., et al., J. Virol., 77: 1621-1625 (2003); Dias, C. C. A., et al., Journal of Interferon & Cytokine Research, 31: 227-236 (2011); Moraes, M. P., et al., Vaccine, 22: 268-279 (2003)). However, this biotherapeutic required a protecting dose approximately 100 times higher than Ad5-based FMDV vaccines (Dias et al., 2011; Pena, L., et al., Vaccine, 26: 5689-5699 (2008)) and the protective activity lasted less than a week. These disadvantages limit its field application. Thus there is a need for a feasible biotherapeutics that can induce rapid and long lasting protection against FMDV which can significantly facilitate the control of the disease during outbreaks.

The type I IFN gene family consists of several subtypes in all mammalian species, and some subtypes contain multiple genes (Roberts, R. M., et al., Interferon Cytokine Res., 18: 805-816 (1998). The antiviral activities of the genes differ a great deal (Moll, H. P., et al., Cytokine, 53: 52-59 (2011)). In pigs, seven subtypes (α, αω, β, δ, ε, κ, and ω) have been reported (Sang, Y., et al., Physiol., 42: 248-258 (2010)), and the antiviral activities against Porcine reproductive and respiratory syndrome virus (PRRSV) and Vesicular stomatitis virus (VSV) infection differ significantly among genes and in different cell lines (Sang et al., 2010; Zanotti, C., et al., J. Interferon Cytokine Res., 35: 990-1002 (2015)). There are substantial polymorphisms in the genes among individuals, which account for significant differences in antiviral activity among the genes (Sang, Y., et al., BMC, 5: S8 (2011)). These results indicate that it is important in terms of biotherapeutic potency to screen a large number of genes and to test in multiple cell lines in order to identify genes with the highest virus-specific antiviral activity.

We previously developed a (3-(4, 5-dimethylthiazolyl-2-yl)-2, 5-diphenyltetrazolium bromide) colorimetric cytopathic effect reduction assay (MTT-CPER assay) to measure anti-FMDV activity (Ramanathan, P., et al., Veterinary Immunology and Immunopathology, 164: 74-78 (2015)). This MTT-CPER assay is more cost-effective, has higher throughput, is less labor intensive, and is more sensitive than the plaque reduction assay. FMDV-susceptible porcine cell lines are used in the assay to measure anti-FMDV specific activity. We used this assay to compare the antiviral activities of porcine IFN expressed in-vitro to identify the best IFN gene, to test the effect of Suppressor Of Cytokine Signaling 1 (SOCS1) gene on IFN expression in order to improve the existing IFN biotherapeutics, and to measure anti-FMDV activity in pigs after treatments. After testing the effect of various techniques on IFN production, we applied the promising ones to produce a new recombinant adenovirus for testing in pigs.

SUMMARY OF THE INVENTION

Disclosed herein is a recombinant adenovirus genome, said adenovirus genome comprising a heterologous nucleic acid inserted into a cloning site of said genome, said heterologous nucleic acid comprising:
a. a first nucleic acid sequence comprising an adenovirus tripartite sequence (e.g., SEQ ID NO:1) operably linked to a second nucleic acid sequence encoding an interferon (e.g., SEQ ID NO:2);
b. a third nucleic acid sequence comprising a bovine growth hormone polyA termination sequence operably linked to said second nucleic acid sequence (e.g., SEQ ID NO:3);
c. a fourth nucleic acid sequence comprising a porcine elongation factor 1-alpha (EF1α) promoter (e.g., SEQ ID NO:4);
d. a fifth nucleic acid sequence operably linked to said fourth nucleic acid sequence, said fifth nucleic acid sequence encoding a suppressor of cytokine signaling 1 (SOCS1) protein (e.g., SEQ ID NO:5).

Also disclosed is a host cell comprising the adenovirus genome.

In addition, there is disclosed a recombinant virus produced by the recombinant adenovirus genome.

Furthermore, there is disclosed a method of producing interferon in an animal (e.g., swine) comprising, introducing into said animal an effective amount of the recombinant virus.

Also disclosed is a method of producing interferon in tissue culture comprising, growing a cell comprising the adenovirus genome under in vitro conditions allowing for the production of interferon, thereby producing interferon.

In addition, there is disclosed an immunomodulatory composition comprising the recombinant virus and a veterinary or pharmaceutically acceptable carrier.

This summary is provided to introduce a selection of concepts in a simplified form that are further described below in the detailed description. This summary is not intended to identify key features or essential features of the

BRIEF DESCRIPTION OF THE DRAWINGS

Exemplary

Exemplary

Exemplary

Exemplary

Exemplary

Exemplary

Exemplary

Exemplary

Exemplary

Exemplary FIG. 10 shows the sequences of three porcine EF1α promoters as described below.

Exemplary

Exemplary

Exemplary

Exemplary

Exemplary

Exemplary

Exemplary

BRIEF DESCRIPTION OF THE SEQUENCES

Figure 1:
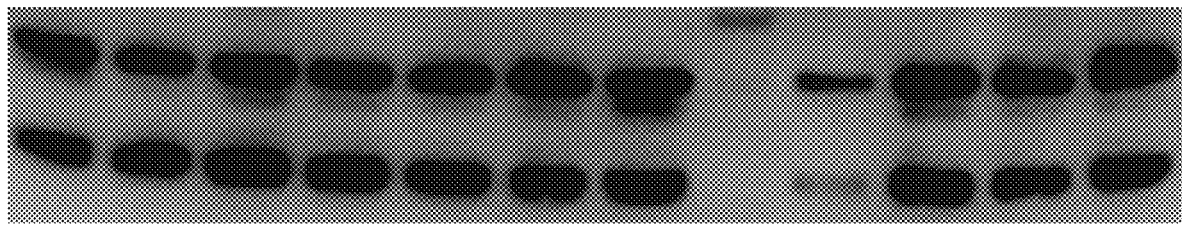
FIG. 1 shows western blotting of supernatants from cultured LFBK-αvβ6 transfected with pcDNA3.1 plasmids inserted with porcine interferon α genes or plasmid vector only (Lane 1-7 and 10-12: IFNα; Lane 8: Protein molecular weight markers, Lane 9: plasmid vector) as described below.

```
SEQ ID NO. 1:
ACTCTCTTCGCATCGCTGTCTGCGAGGGCGAGCTGTTGGGCTCGCGGTTGA

GGACAAACTCTTCGCGGTCTTTCCAGTACTCTTGGATCGGAAACCCGTCGG

CCTCCGAACGGTACTCCGCCACCGAGGGACCTGAGCGGTCCGCATCGACCG

GATCGGAAAACCTCTCGAGAAAGGCGTCTAACCAGTCACAGTCGCAAG is
adenovirus Ad5 tripartite sequence (Zhang Y., et
al., J. Biol. Chem., 264(18): 10679-84 (1989)).
```

SEQ ID NO. 2:
ATGGCTCCCACCTCCGCCTTCCTGACCGTGCTGGTGCTGCTGAGCTGCAAC

GCCATCTGCTGCCTGGGATGCGACCTGCCACAGACCCACTCCCTGGCTCAC

ACCAGGGCCCTGAGACTGCTGGCTCAGATGAGGAGGATCTCCCCCTTCAGC

TGCCTGGACCACAGGAGAGACTTCGGCAGCCCACACGAGGCCTTCGGCGGA

AACCAGGTGCAGAAGGCTCAGGCTATGGCCCTGGTGCACGAGATGCTGCAG

CAGACCTTCCAGCTGTTCTCCACCGAGGGCAGCGCCGCCGCCTGGGACGAG

TCCCTGCTGCACCAGTTCTGCACCGGCCTGGACCAGCAGCTGCGCGACCTG

GAGGCCTGCGTGATGCAGGAGGCTGGCCTGGAGGGCACCCCACTGCTGGAG

GAGGACAGCATCCTGGCCGTGCGCAAGTACTTCCACCGGCTGACCCTGTAC

CTGCAGGAGAAGTCCTACAGCCCATGCGCTTGGGAGATCATCAGGGCTGAA

GTGATGAGAGTGTTCAGCTCCAGCCGGAACCTGCAGGACAGGCTGCGGAAG

AAGGAGTGA is a porcine interferon alpha codon
optimized from GQ415066 (IFN19).

SEQ ID NO. 3:
GCGGCCGCCTGTGCCTTCTAGTTGCCAGCCATCTGTTGTTTGCCCCTCCCC

CGTGCCTTCCTTGACCCTGGAAGGTGCCACTCCCACTGTCCTTTCCTAATA

AAATGAGGAAATTGCATCGCATTGTCTGAGTAGGTGTCATTCTATTCTGGG

GGGTGGGGTGGGGCAGGACAGCAAGGGGGAGGATTGGGAAGACAATAGCAG

GCATGCTGGGGATGCGGTGGGCTCTATG is a bovine growth
hormone polyA termination sequence.

SEQ ID NO. 4:
GCGGAGAGTAATTCATACAAAAGGAGGACTCTCCTCAGCCAGGGAAATCC

CAGGGACCGTCGATAAACTCCCACTAAACCTAGAACCGAGTGAGCGCTCG

ACCCCGCCTCCCACCCACCAGCAGTCGTCATCCTCCTGGTTGAGAGGAGC

ATGCGCCGGGCGCCGTGTGCTCGTCAGTGGGCTGAACGCACATCGCCCAC

GGTCCCCGAAGATGGGGGAGGGGACGGCGGTGGAACCGGTGCCGGGTGG

AGGTGGCGCGGGGTAAACTGGGAAAGTGGTGTCGTGTGCTGGCTCCGCCC

TTTTCCCCGAGGGTGGGGGAGGACCATATATAAGCGCCGTGGTCCCCGCG

AACGTTCTTTTTCGCAACGGGTTTGCCGCCAGGACACAGGTGAGTACGGG

TGTGGCCTCCGTCCGCATGGCCTCCGCCGGTGGCCACGGCCTTAGCGTGC

CTCCCGGCCCCCGCGCGTAGAGGGCTCTGCGCCCTGGTCCTGATTCCGA

GCTGCGGGCGGGGGAGGTGGAGAACTCGAGGCCCTCCGCTCTCGCGGTT

CCCTACCGCGTGCCCGGTGGCGGCCTGCTGGGGCGCCGTGGCCGCCGCGT

GCGATCCGCGCCTTCGCGCCCGGTCGTCGGGACAGTAGTATAAATAAGGT

TTTTGTCGTCTTAGGTGTCGTGAAAGCCATCGCTAAAAGCT is a
porcine elongation factor 1-alpha (EF1α) promoter.

SEQ ID NO. 5:
ATGGTGGCTCACAACCAGGTGGCTGCTGACAACGCCATCAGCACCGCTGC

TGAGCCACGCCGGAGGCCCGAGCACAGCTCCAGCTCCAGCTCCAGCTCCA

GCTCCAGCTCCAGCTCCAGCTCCCCCGGCGTGCCCGCCCGGCCCAGGCCC

TGCCCAGCTGCCCCGCTCCAGCTCCAGGCGACACCCACTTCCGGACCTT

CAGGAGCCACGCCGACTACAGAAGGATCACCAGGGCCTCCGCCCTGCTGG

ACGCTTGCGGCTTCTACTGGGGACCACTGTCCGTGCACGGCGCTCACGAG

AGACTGAGGGCTGAGCCCGTGGGCACCTTCCTGGTGAGAGACAGCCGGCA

GAGGAACTGCTTCTTCGCTCTGTCCGTGAAGATGGCCAGCGGACCCACCT

CCATCAGAGTGCACTTCCAGGCTGGCCGCTTCCACCTGGACGGCAGCCGG

GAGTCCTTCGACTGCCTGTTCGAGCTGCTGGAGCACTACGTGGCTGCTCC

AAGGAGGATGCTGGGAGCTCCACTGAGACAGAGACGCGTGCGCCCCCTGC

AGGAGCTGTGCAGACAGAGGATCGTGGCTACCGTGGGAAGGGAGAACCTG

GCTCGCATCCCCCTGAACCCCGTGCTGCGGGACTACCTGAGCTCCTTCCC

CTTCCAGATTTGA is a porcine suppressor of cytokine
signaling 1 (SOCS1) open reading frame sequence
codon-optimized from NM_001204768.

SEQ ID NO. 6:
ATCGATACTCTCTTCGCATCGCTGTCTGCGAGGGCGAGCTGTTGGGCTCG

CGGTTGAGGACAAACTCTTCGCGGTCTTTCCAGTACTCTTGGATCGGAAA

CCCGTCGGCCTCCGAACGGTACTCCGCCACCGAGGGACCTGAGCGGTCCG

CATCGACCGGATCGGAAAACCTCTCGAGAAAGGCGTCTAACCAGTCACAG

TCGCAAGCTAGCCACCATGGCTCCCACCTCCGCCTTCCTGACCGTGCTGG

TGCTGCTGAGCTGCAACGCCATCTGCTGCCTGGGATGCGACCTGCCACAG

ACCCACTCCCTGGCTCACACCAGGGCCCTGAGACTGCTGGCTCAGATGAG

GAGGATCTCCCCCTTCAGCTGCCTGGACCACAGGAGAGACTTCGGCAGCC

CACACGAGGCCTTCGGCGGAAACCAGGTGCAGAAGGCTCAGGCTATGGCC

CTGGTGCACGAGATGCTGCAGCAGACCTTCCAGCTGTTCTCCACCGAGGG

CAGCGCCGCCGCCTGGGACGAGTCCCTGCTGCACCAGTTCTGCACCGGCC

TGGACCAGCAGCTGCGCGACCTGGAGGCCTGCGTGATGCAGGAGGCTGGC

CTGGAGGGCACCCCACTGCTGGAGGAGGACAGCATCCTGGCCGTGCGCAA

GTACTTCCACCGGCTGACCCTGTACCTGCAGGAGAAGTCCTACAGCCCAT

GCGCTTGGGAGATCATCAGGGCTGAAGTGATGAGAGTGTTCAGCTCCAGC

CGGAACCTGCAGGACAGGCTGCGGAAGAAGGAGTGAGCGGCCGCCTGTGC

CTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGG

GGCAGGACAGCAAGGGGGAGGATTGGGAAGACAATAGCAGGCATGCTGGG

GATGCGGTGGGCTCTATGGCGGAGAGTAATTCATACAAAAGGAGGACTCT

CCTCAGCCAGGGAAATCCCAGGGACCGTCGATAAACTCCCACTAAACCTA

GAACCGAGTGAGCGCTCGACCCCGCCTCCCACCCACCAGCAGTCGTCATC

CTCCTGGTTGAGAGGAGCATGCGCCGGGCGCCGTGTGCTCGTCAGTGGGC

TGAACGCACATCGCCCACGGTCCCCGAAGATGGGGGAGGGGACGGCGGT

GGAACCGGTGCCGGGTGGAGGTGGCGCGGGGTAAACTGGGAAAGTGGTGT

CGTGTGCTGGCTCCGCCCTTTTCCCCGAGGGTGGGGGAGGACCATATATA

AGCGCCGTGGTCCCCGCGAACGTTCTTTTTCGCAACGGGTTTGCCGCCAG

GACACAGGTGAGTACGGGTGTGGCCTCCGTCCGCATGGCCTCCGCCGGTG

GCCACGGCCTTAGCGTGCCTCCCGGCCCCCGCGCGTAGAGGGCTCTGCG

CCCTGGTCCTGATTCCGAGCTGCGGGCGGGGGAGGTGGAGAACTCGAGG

-continued

```
CCCTCCGCTCTCGCGGTTCCCTACCGCGTGCCCGGTGGCGGCCTGCTGGG
GCGCCGTGGCCGCCGCGTGCGATCCGCGCCTTCGCGCCCGGTCGTCGGGA
CAGTAGTATAAATAAGGTTTTTGTCGTCTTAGGTGTCGTGAAAGCCATCG
CTAAAAGCTGCTAGTCACCATGGTGGCTCACAACCAGGTGGCTGCTGACA
ACGCCATCAGCACCGCTGCTGAGCCACGCCGGAGGCCCGAGCACAGCTCC
AGCTCCAGCTCCAGCTCCAGCTCCAGCTCCAGCTCCAGCTCCCCCGGCGT
GCCCGCCCGGCCCAGGCCCTGCCCAGCTGCCCCCGCTCCAGCTCCAGGCG
ACACCCACTTCCGGACCTTCAGGAGCCACGCCGACTACAGAAGGATCACC
AGGGCCTCCGCCCTGCTGGACGCTTGCGGCTTCTACTGGGGACCACTGTC
CGTGCACGGCGCTCACGAGAGACTGAGGGCTGAGCCCGTGGGCACCTTCC
TGGTGAGAGACAGCCGGCAGAGGAACTGCTTCTTCGCTCTGTCCGTGAAG
ATGGCCAGCGGACCCACCTCCATCAGAGTGCACTTCCAGGCTGGCCGCTT
CCACCTGGACGGCAGCCGGGAGTCCTTCGACTGCCTGTTCGAGCTGCTGG
AGCACTACGTGGCTGCTCCAAGGAGGATGCTGGGAGCTCCACTGAGACAG
AGACGCGTGCGCCCCCTGCAGGAGCTGTGCAGACAGAGGATCGTGGCTAC
CGTGGGAAGGGAGAACCTGGCTCGCATCCCCCTGAACCCCGTGCTGCGGG
ACTACCTGAGCTCCTTCCCCTTCCAGATTTGATCTAGA is the
nucleotide sequence inserted in plasmid Ad5 Blue
vector between restriction sites ClaI and XhaI.
```

DETAILED DESCRIPTION OF THE INVENTION

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

The term a nucleic acid or protein "consisting essentially of", and grammatical variations thereof, means: 1) nucleic acids that differ from a reference sequence by 20 or fewer nucleic acid residues and also perform the function of the reference nucleic acid sequence, and 2) proteins that differ from a reference sequence by 10 or fewer nucleic acids and also perform the function of the reference protein sequence. Such variants include sequences which are shorter or longer than the reference sequence, have different residues or amino acids at particular positions, or a combination thereof.

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

In practicing some embodiments of the invention disclosed herein, it can be useful to modify the genome of a recombinant strain of a virus producing the interferon or other proteins of the immunogenic compositions. In preferred embodiments, the virus is an adenovirus. Such modification can involve deletion of all or a portion of a target gene or regulatory sequence, such as a promoter, including but not limited to the open reading frame of a target locus, transcriptional regulators such as promoters of a target locus, and any other regulatory nucleic acid sequences positioned 5' or 3' from the open reading frame. Such deletional mutations can be achieved using any technique known to those of skill in the art. Mutational, insertional, and deletional variants of the disclosed nucleotide sequences and genes can be readily prepared by methods which are well known to those skilled in the art. It is well within the skill of a person trained in this art to make mutational, insertional, and deletional mutations which are equivalent in function to the specific ones disclosed herein.

Where a recombinant nucleic acid is intended for expression, cloning, or replication of a particular sequence, DNA constructs prepared for introduction into a viral genome will typically comprise a replication system (i.e., vector) recognized by a target host or viral replication machinery, including the intended DNA fragment encoding a desired polypeptide, and can also include transcription and translational initiation regulatory sequences operably linked to a polypeptide-encoding segment. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Expression systems can comprise a recombinant viral genome, such that the modified virus is produced following introduction of a vector containing the genome of the virus, or several vectors which, in combination, comprise the genome of the recombinant virus which is then reconstituted upon introduction into a host cell and expression of the recombinant genome.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Additionally, screening and molecular analysis of genetically altered viruses, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., Science, 230:1350-1354 (1985)). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology (identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul, Proc. Natl. Acad. Sci. USA, 87:2264-2268 (1990), modified as in Karlin and Altschul, Proc. Natl. Acad. Sci. USA, 90:5873-5877 (1993). Such an algorithm is incorporated into the NBLAST and) (BLAST programs of Altschul et al., J. Mol. Biol., 215:402-410 (1990). BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al., Nucl. Acids. Res., 25:3389-3402 (1997). When utilizing BLAST and Gapped BLAST programs, the default parameters of the respective programs (NBLAST and)(BLAST) are used. See www.ncbi.nih.gov.

In practicing the disclosure herein, any suitable bacterial, protist, animal or fungal host capable of allowing replication of the virus or its genome can be utilized. Even more preferably, non-pathogenic and non-toxigenic strains of such host cells are utilized in practicing embodiments of the disclosed inventions. Examples of workable combinations of cell lines and expression vectors are described in Sambrook et al. (1989); Ausubel et al. (Eds.) (1995) Current Protocols in Molecular Biology, Greene Publishing and Wiley Interscience, New York; and Metzger et al., Nature, 334: 31-36 (1988). The nucleic acid(s) encoding the viruses and protein(s) of the present invention can be introduced by any means known to the art which is appropriate for the particular type of cell, including without limitation, transformation, lipofection, electroporation or any other methodology known by those skilled in the art.

Other compounds (e.g., a known immunomodulating agent) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising a known immunomodulating agent" means that the composition may or may not contain a known immunomodulating agent and that this description includes compositions that contain and do not contain a known immunomodulating agent. Also, by example, the phrase "optionally adding a known immunomodulating agent" means that the method may or may not involve adding a known immunomodulating agent and that this description includes methods that involve and do not involve adding a known immunomodulating agent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41 (1): 46-47 (2013): " . . . Written support for a negative limitation may also be argued through the absence of the excluded element in the specification, known as disclosure by silence . . . Silence in the specification may be used to establish written description support for a negative limitation. As an example, in Ex parte fin [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation . . . ."

In preferred embodiments of the present disclosure, the virus utilized is an adenovirus that comprises an adenoviral vector (e.g., Ad5 Blue) encoding an exogenous gene construct. In preferred embodiments of the present invention it is contemplated that the exogenous gene construct encodes a protein that interferes with FMDV. Typically, a gene construct (e.g., interferon) is operatively linked to a promoter (e.g., human Cytomegalovirus promoter). In particular embodiments, another promoter (porcine EF1α promoter) is inserted in the 3' end of the gene transcribed by the CMV promoter in order to express another protein that can enhance the expression of the gene transcribed by CMV promoter. In practicing the present disclosure, an adenovirus can be a replication-incompetent adenovirus. In such embodiments, host cells capable of complementing replication can be utilized, such as HEK 293 cells and other appropriate cells known in the art.

In certain aspects of the present invention, host cells may be harvested and lysed ex situ using a hypotonic solution, hypertonic solution, freeze-thaw, sonication, impinging jet, microfluidization or a detergent. In other aspects, the cells are harvested and lysed in situ using a hypotonic solution, hypertonic solution, or a detergent (e.g., Tween-20®, Brij-58®, Triton X®-100 or octyl glucoside). Cells can also be lysed through autolysis of infected cells. Virus collection from tissue culture can utilize any methodology known in the art. As used herein the term "in situ" refers to the cells being located within a tissue culture apparatus and "ex situ" refers to the cells being removed from the tissue culture apparatus.

Modified viruses described herein can be administered to a target animal (e.g., swine) by intramuscular, subcutaneous, or intranasal inoculation, or injection in an amount which is effective to protect the animal against challenge by a virulent strain of viruses such as FMDV, or induce the production of a protective amount of interferon. This amount may vary according to the animal being inoculated, taking into consideration the size and weight of the animal. The viruses according to the invention comprise an effective dosage of the interferon-expressing genomes to induce a significantly higher level of protection in a recipient animal population against mortality and clinical symptoms of FMDV compared to untreated animals. In particular, the recombinant viruses according to the invention prevents a proportion of animals vaccinated against FMDV from developing symptoms prior to the onset of protective immunity. Typically, the viruses are administered in a dose of $10^9$-$10^{10}$ PFU, but other doses can be utilized. Effective amounts may be experimentally determined as necessary by those of skill in the art by following the guidance provided herein, or by any methodology known in the art.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Cells and viruses: Immortalized LFBK-αvβ6 kidney cells (LaRocco, M., et al., J. Clin. Microbiol., 51: 1714-1720 (2013); Swaney, L. M., Vet. Microbiol., 18: 1-14 (1988)), IBRS-2 kidney cells (House, J. A., et al., Journal of the Tissue Culture Association, 24: 677-682 (1988)), and HEK 293 cells (Graham, F. L., et al., J. Gen. Virol., 36: 59-74 (1977)) were obtained from the Foreign Animal Disease Diagnostic Laboratory at the Plum Island Animal Disease Center. The LFBK-αvβ6 cells were cultured in Dulbecco's Modified Eagle medium (DMEM, GIBCO, Grand Island, N.Y.) containing high glucose, 10% fetal bovine serum (FBS) (HyClone, Logan, Utah), and supplemented with 1% Antibiotics-Antimycotic 100X (GIBCO) and 1% Sodium Pyruvate 100X (GIBCO). The IBRS-2 and HEK 293 cells were grown in Minimum Essential Medium (MEM, GIBCO) with 10% FBS, 1% L-Glutamine, 1% Antibiotics, and Non-Essential Amino Acids 100X (GIBCO). All cell culture media and reagents were purchased from Life Technologies (Carlsbad, Calif.) unless specified otherwise. FMDV type A24 Cruzeiro strain was produced in baby hamster kidney (BHK) cells and used in this study.

Interferon protein Expression: Full-length coding sequences of 19 porcine IFNα and 5 IFNβ genes were identified from the pig genome sequences released in August 2011 (SGSC Sscrofa10.2/susScr3 Assembly) using the UCSC Genome Browser. Additionally, 13 IFNα coding sequences of miniature pigs were retrieved from the genomic sequences deposited in NCBI GenBank from Accession #: PRJNA176189, AJKK01153980, AJKK01221111, AJKK01220487, AJKK01240321, AJKK01266018, AJKK01153977, and AJKK01148380. These 37 coding DNA sequences with a Kozak sequence of GCCACC in the 5' end of ATG and NheI and NotI restriction site sequences in both ends were cloned into pcDNA3.1-vector (Life Technologies) between the NheI and NotI restriction sites. The plasmids containing the inserts of interests as well as a vector only control were purified with Qiagen plasmid miniprep kits (Qiagen) and were transiently transfected into LFBK-αvβ6 cells for the expression of their respective porcine IFN proteins using Lipofectamine 2000 (ThermoFisher Scientific). The cell culture supernatants were harvested at days 2 and 4 post-transfection and stored at −70° C. until assayed. The expressed IFN proteins were detected with Western blotting using a rabbit anti-porcine IFN-α antibody and the WesternDot 625 Goat Anti-Rabbit Western Blot Kit (ThermoFisher Scientific). The imaging was performed using a GelDoc imager (BioRad).

MTT-CPER assay: The anti-FMDV activity of the harvested cell culture supernatants was measured with an MTT-CPE reduction (MTT-CPER) assay we developed (Ramanathan et al., 2015). Briefly, IBRS-2 and/or LFBK-αvβ6 cells were plated in 96-well flat-bottomed tissue culture plates to 100% confluency after overnight incubation. Then the cells were treated with two-fold serially diluted cell culture supernatants harvested from the cells transfected with plasmid DNA or infected with Ad5 recombinant viruses. After 18 hours of incubation, the IFN-containing media were removed and the cells were inoculated with FMDV A24 Cruzeiro at a multiplicity of infection (MOI) of 0.4 for 22-hour incubation. A MTT (3-(4, 5-dimethylthiazolyl-2-yl)-2, 5-diphenyltetrazolium bromide) substrate (ATCC, Manassas, Va.) was added to each well and the plates were stored in the dark for 3 hours. Then a detergent reagent provided by ATCC was added to each well for another 3 hours incubation at room temperature before spectrometry. The absorbance or optical density (OD) readings in each well was measured using an ELx808 Absorbance Microplate Reader at 570 nm with the reference filter set at 650 nm (BioTek, Winooski, Ver.). The blank values were subtracted from the absorbance values. There were three technical replicates per sample in the assays. The OD readings were used as the indicator of anti-FMDV activity (cells protected by IFN against FMDV infection).

For the determination of anti-FMDV activity of the genes and the recombinant adenovirus, the OD readings were fit to a sigmoid dose-response curve using GraphPad Prism software package (PBL Assay Science, Piscataway, N.J.). The half maximal effective concentration (EC50) used as the indicator of anti-FMDV activity were calculated using the software based on the fold dilutions of the supernatants and the OD readings of the culture wells. IFN gene GQ415066/IFN19 was used as a reference in all DNA transfections and antiviral assays for comparison among the genes. The gene with the highest anti-FMDV activity was given an arbitrary index number of 1 as an anti-FMDV activity. The EC50 of other genes was divided by the gene with the highest activity to normalize the antiviral activity. Differences in anti-FMDV activity between the Ad5 viruses created in this study and the Ad5 viruses tested previously were calculated by taking both MOI and EC50 into account.

Effect of NCS on IFNα production: An interferon α coding sequence (NM_001172040) was cloned into pcDNA3.1-vector (Life Technologies) between the NheI and NotI restriction sites and named as pcDNA3.1-IFNα. To test the effect of NCS on IFN production, an adenovirus tripartite sequence (Kaufman 1985; Logan and Shenk 1984; Zhang et al 1989) was placed in the 5' ends of the IFNα coding sequence and inserted into pcDNA3.1 plasmid between NheI and NotI restriction sites. All plasmids were purified with Qiagen plasmid miniprep kits (Qiagen, Germantown, Md.). The plasmid inserted with the IFNα coding sequence only was used as the control. These plasmids were transfected with equal amounts of DNA into LFBK-αvβ6 cells using Lipofectamine 2000 (ThermoFisher Scientific). After DNA transfection, the supernatants were harvested for MTT-CPER assay as described above at days 2, 4 and 6 post-transfection and stored at −70° C. until assayed. All inserted DNA including these described in the following were synthesized by GenScript (Piscataway, N.J.).

Effect of SOCS1 (suppressor of cytokine signaling 1) on IFNα production: To test the effect of SOCS1 on IFN production, the porcine SOCS1 coding sequence (NM_001204768) was inserted into the pcDNA3.1 plasmid between NheI and NotI restriction sites. The plasmid containing a SOCS1 gene was used to co-transfect LFBK-αvβ6 cells with a pcDNA3.1 plasmid inserted with the interferon α gene at 1:1 and 1:3 (pcDNA3.1-IFNα vs pcDNA3.1-SOCS1) of DNA using the transfection procedure described earlier. A co-transfection with the same amount of plasmid pcDNA3.1 vector without inserts and the plasmid inserted with the interferon gene was used as the control to assess the effect of the SOCS1 gene on the interferon expression. After DNA transfection, the supernatants were harvested for MTT-CPER assay as described above.

Transcription activity of EF1α Promoters: To insert two genes into the Ad5-blue vector, we designed and constructed two promoters containing MfeI and NheI site sequences in 5' and 3' end, respectively, using the sequences of bovine and porcine EF1α genes. These promoter sequences start from ~350 bp upstream of the transcription start sites to the start codon of EF1α coding sequences. A sequence fragment located within the first intron (579 bp for bovine promoter and 338 bp for the porcine promoter that are less homologous among species) was deleted to reduce the length of the promoters to 760 bp, which are very close to the length of CVM promoter. The pcDNA3.1 plasmid inserted with the interferon α gene between NheI and NotI sites was digested with MfeI and NheI restriction enzymes (New England Biolabs, Ipswich, Mass.) and ligated with MfeI and NheI restriction enzyme digested bovine and/or porcine promoter DNA fragments, which replaced the hCMV promoter of the pcDNA3.1 plasmid vector (pcDNA3.1_hCMV-IFNα). These two plasmids containing bovine and porcine promoters were named as pcDNA3.1_bEF1α-IFNα and pcDNA3.1_sEF1α-IFNα, respectively. These three plasmid DNA samples were used to transfect HEK293 and LFBK-αvβ6 cells to measure anti-FMDV activity induced in the culture supernatants as described earlier.

Figure 2A:
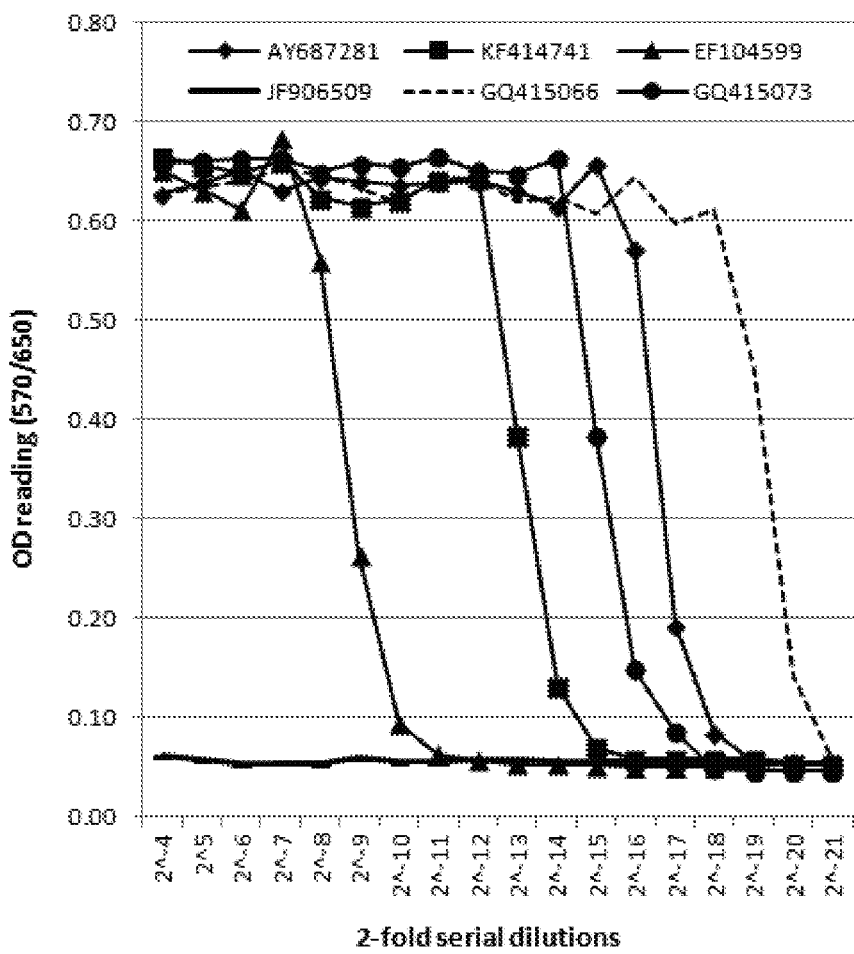
FIG. 2A and FIG. 2B show the optical density (OD) readings of MTT-based CPER assays using IBRS-2 and supernatants harvested from LFBK-αvβ6 cells transfected with plasmid DNA inserted with porcine IFNβ or the best porcine IFNα coding sequences; at Days 2 (FIG. 2A) and 4 (FIG. 2B) post transfection as described below.
Figure 2B:
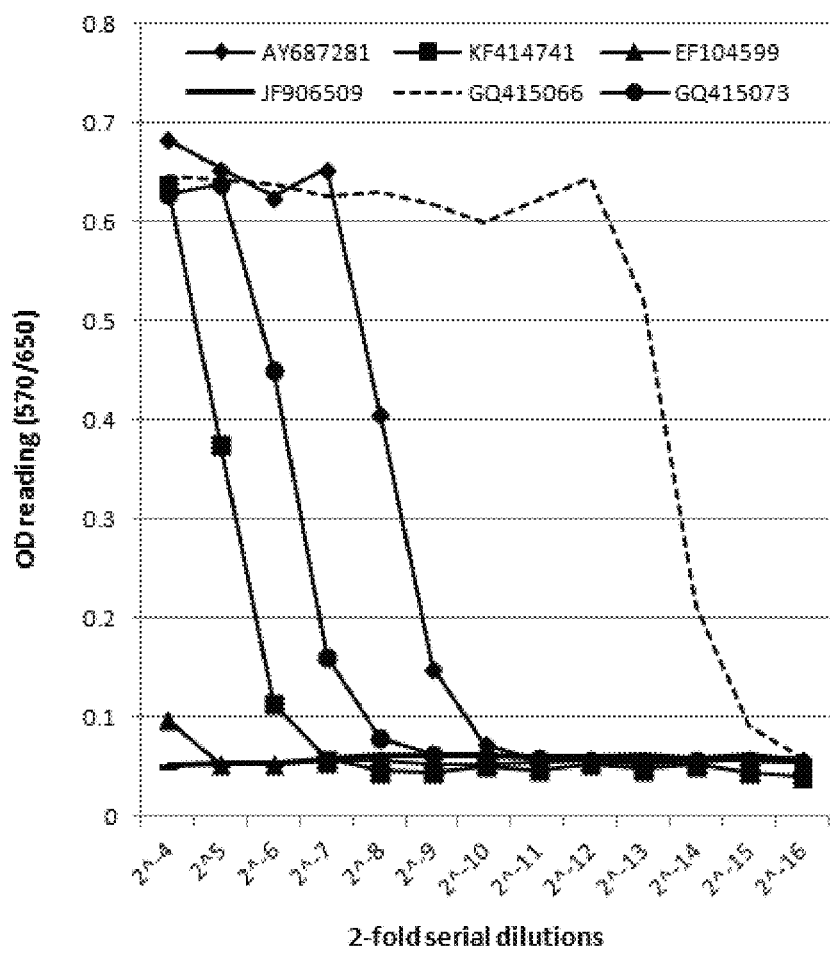
Figure 3:
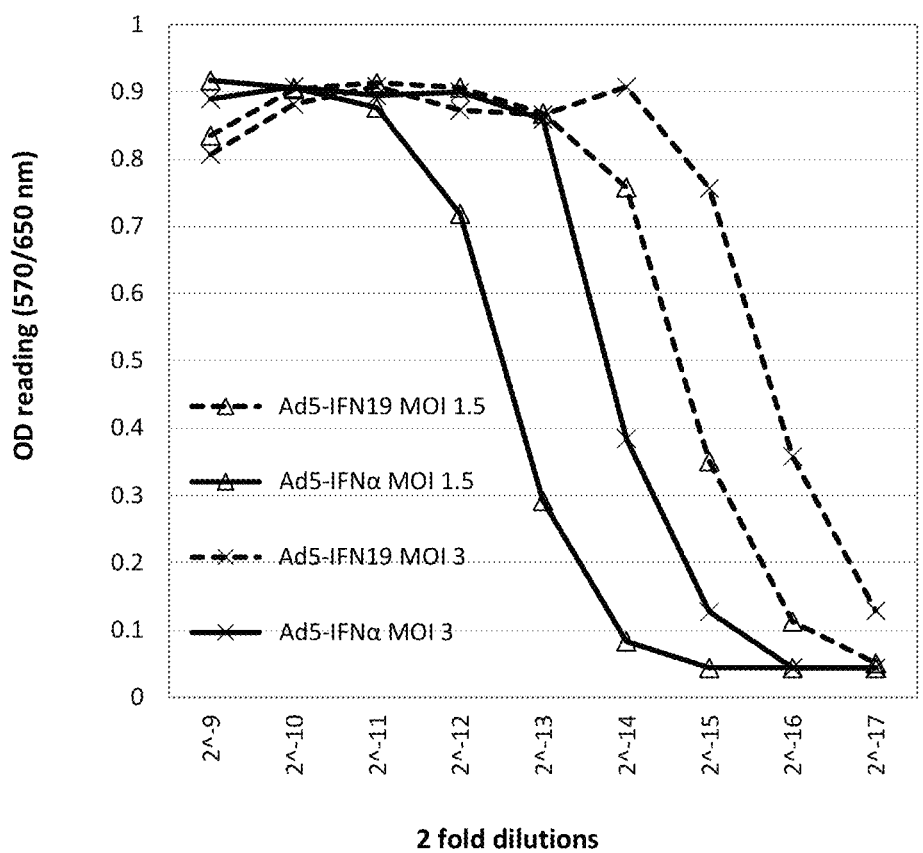
FIG. 3 shows the OD readings of MTT-based CPER assays using LFBK-αvβ6 and supernatants harvested from LFBK-αvβ6 cells infected with two different MOI (multiplicity of infection) of recombinant adenoviruses inserted with the best (Ad5-IFN19) or previously tested interferon (Ad5-IFNα) coding sequences at Day 1 post infection as described below.
Figure 4A:
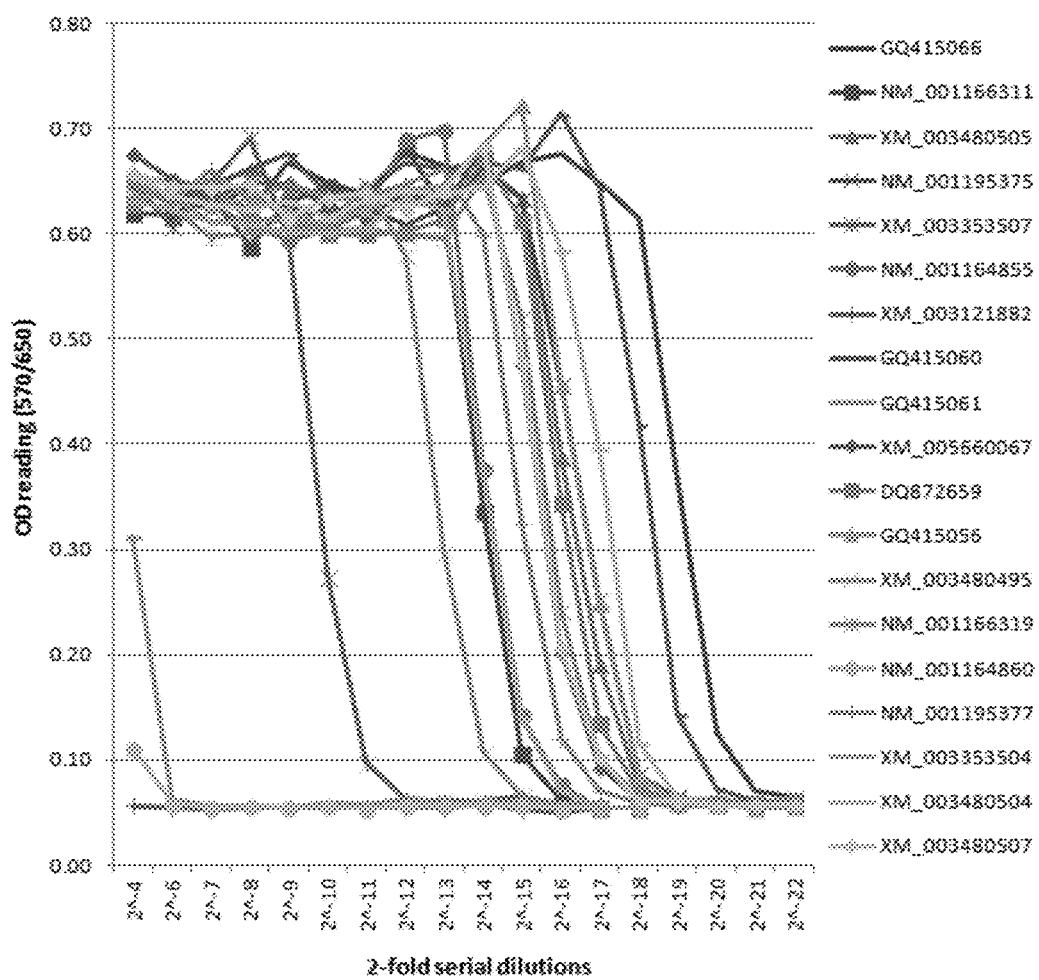
FIG. 4A and FIG. 4B show the OD readings of MTT-based CPER assays using IBRS-2 cells and supernatants harvested from LFBK-αvβ6 cells transfected with plasmid DNA inserted with porcine IFNα coding sequences; at Days 2 (FIG. 4A) and 4 (FIG. 4B) post DNA transfection as described below.
Figure 4B:
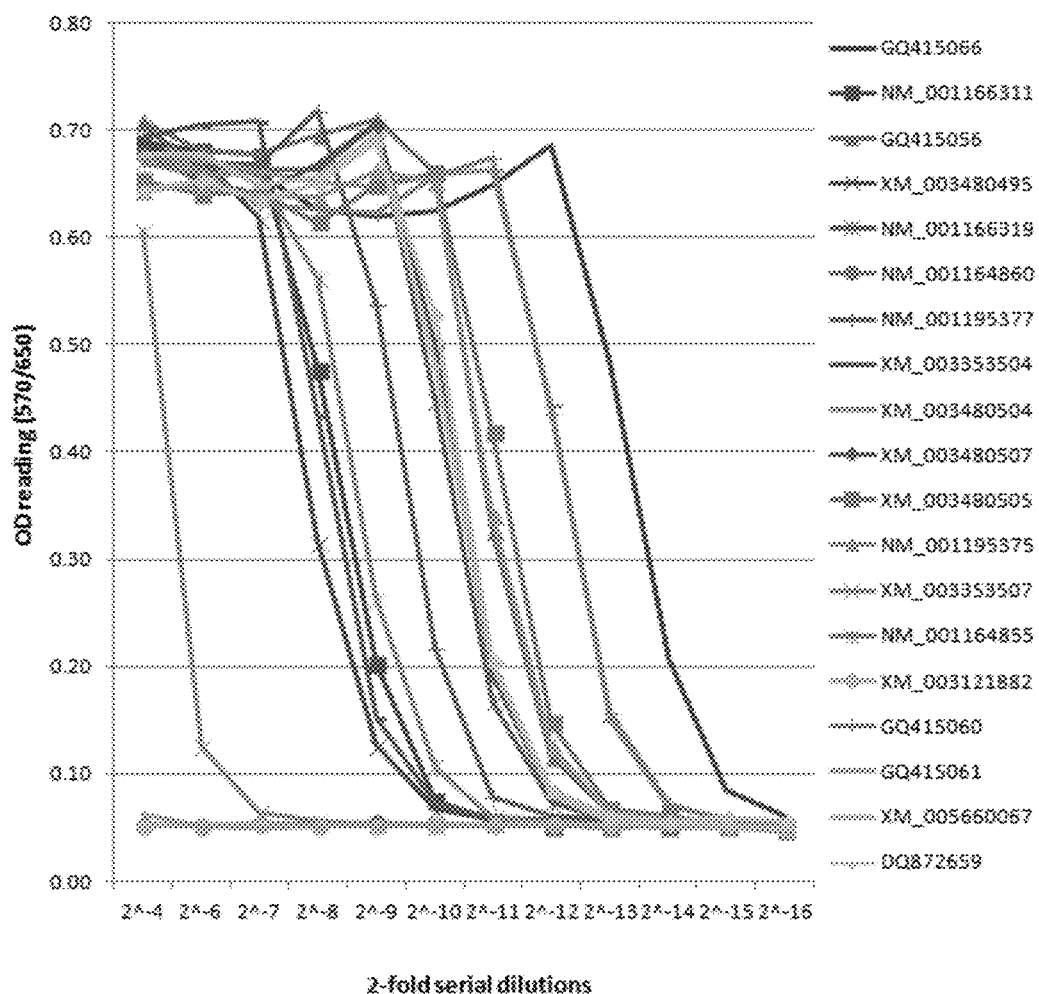
Figure 5A:
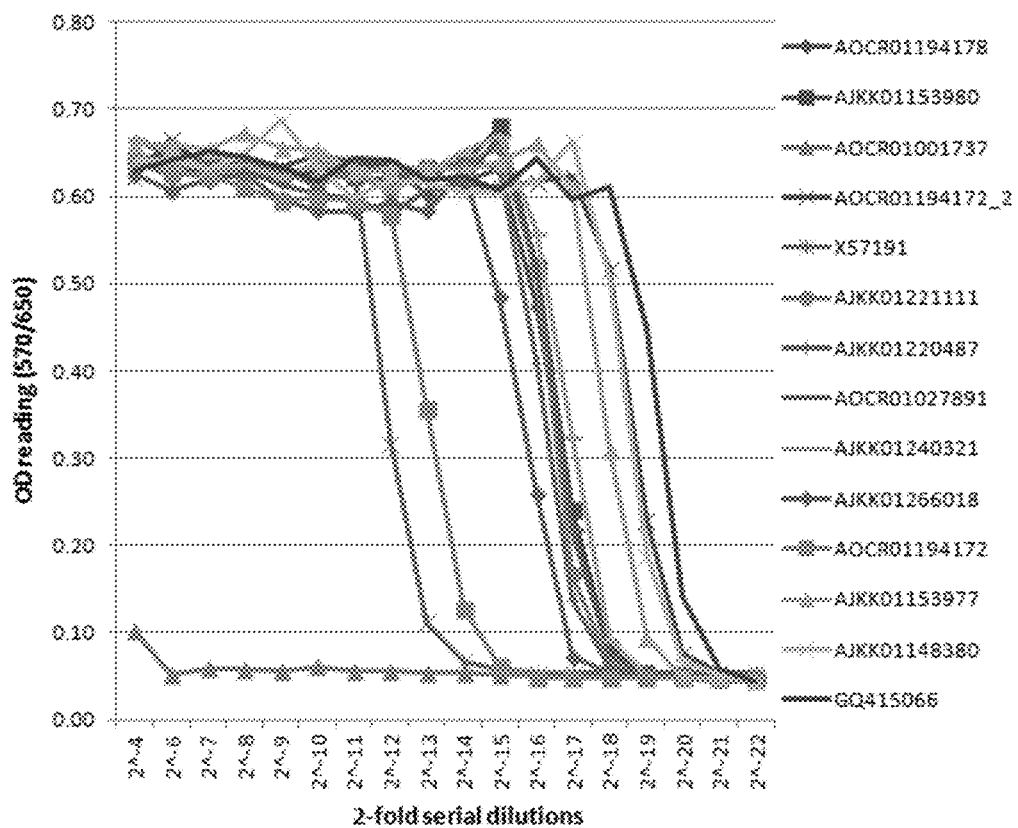
FIG. 5A and FIG. 5B show the OD readings of MTT-based CPER assays using IBRS-2 and supernatants harvested from LFBK-αvβ6 cells transfected with plasmid DNA inserted with the best porcine interferon or miniature pig IFNα coding sequences; at Days 2 (FIG. 5A) and 4 (FIG. 5B) as described below.
Figure 5B:
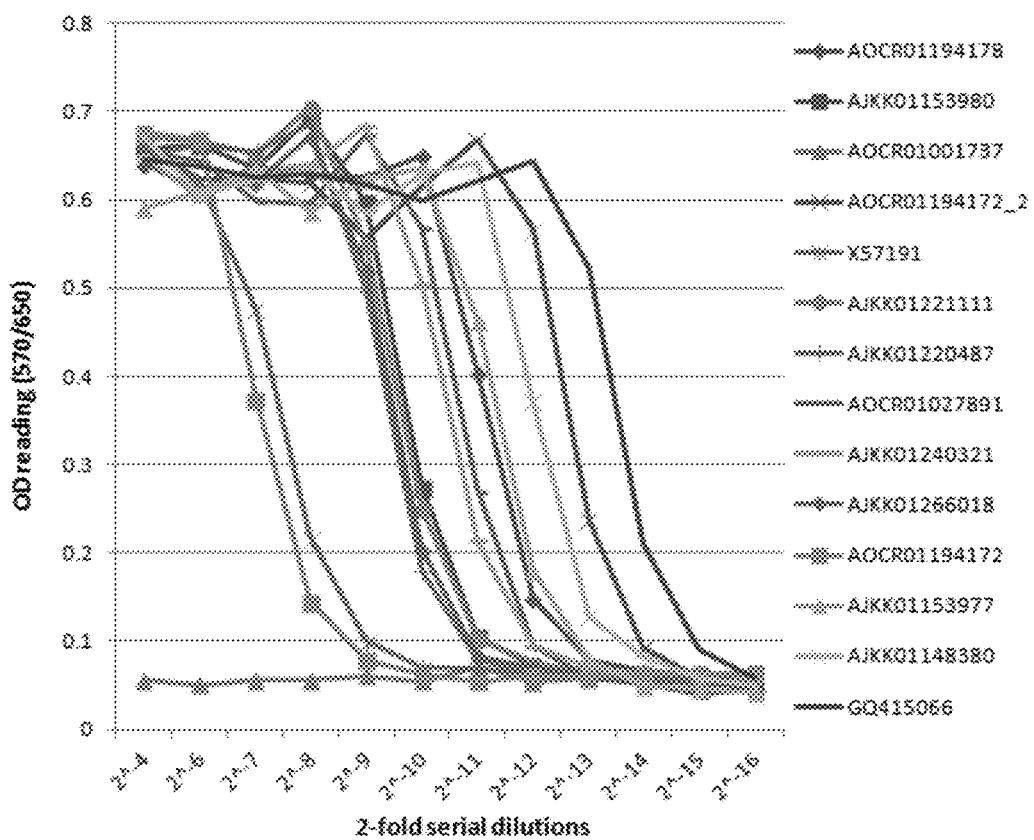
Figure 6:
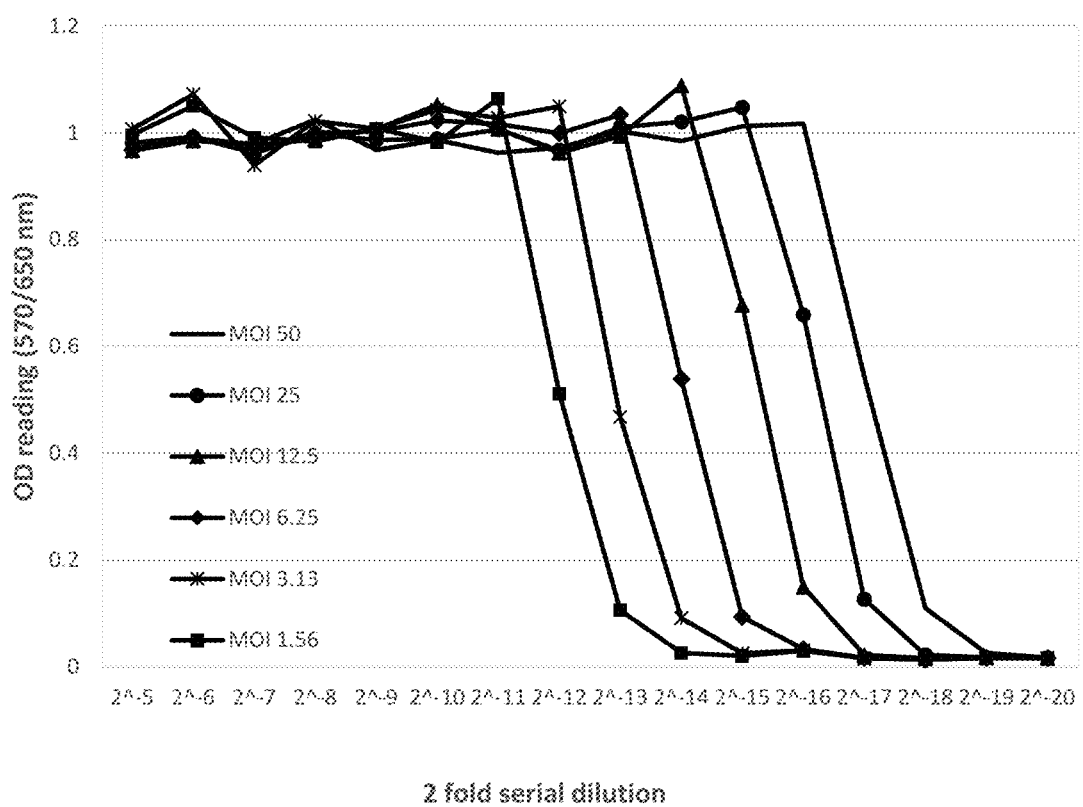
FIG. 6 shows the OD readings of MTT-based CPER assays using LFBK-αvβ6 from supernatants harvested from LPBK-αvβ6 cells infected with different MOI of recombinant adenoviruses Ad5-IFNα post infection as described below.
Figure 7A:
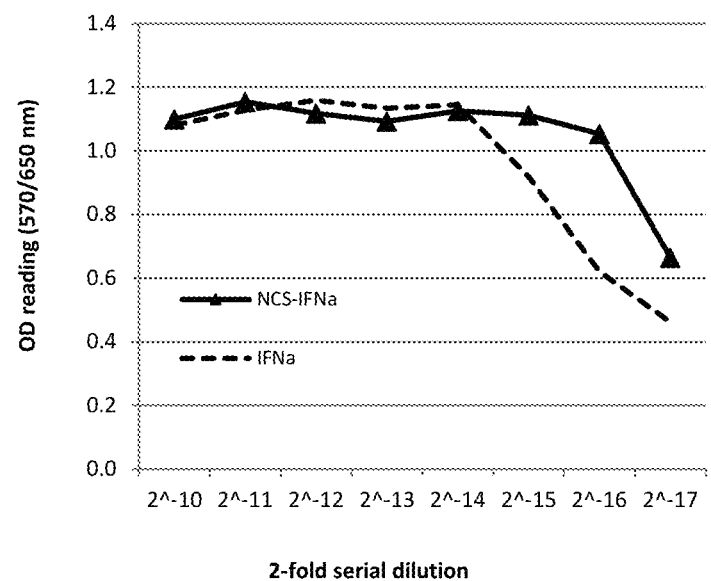
FIG. 7A, FIG. 7B, FIG. 7C, and FIG. 7D show the OD readings of MTT-based CPER assays using LFBK-αvβ6 and supernatants harvested from LFBK-αvβ6 cells co-transfected with plasmid DNA containing an IFNα gene with or without an adenovirus tripartite non-coding sequence (NCS) in the 5'-end of the interferon coding sequence; at days 2 (FIG. 7A), 4 (FIG. 7B) and 6 (FIG. 7C) post-transfection and using supernatants from the cells infected with adenoviruses containing an IFNα gene with or without the NCS at day 6 post infection (FIG. 7D) as described below.
Figure 7B:
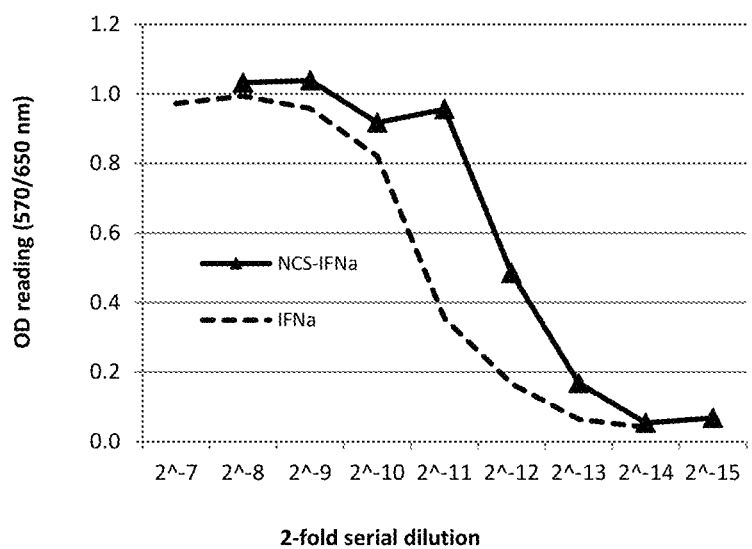
Figure 7C:
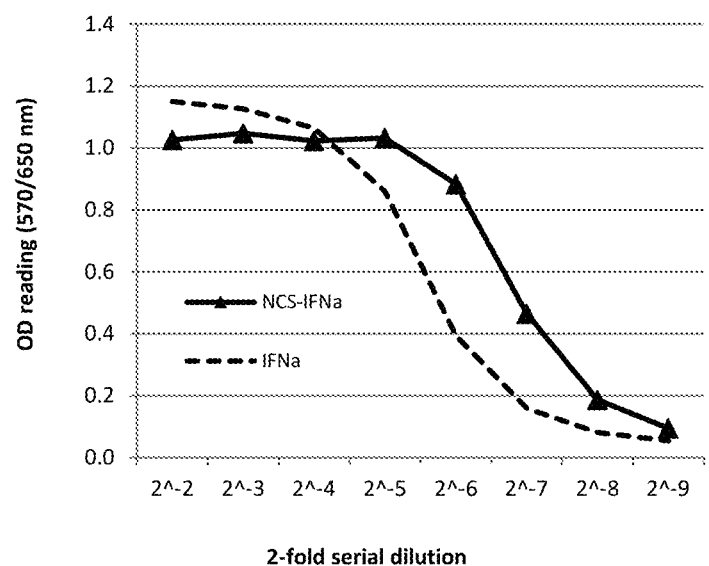
Figure 7D:
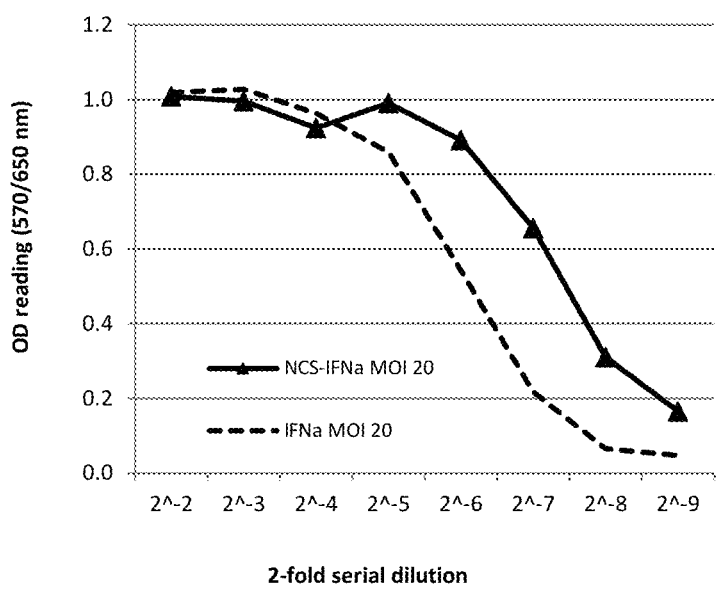
Figure 8A:
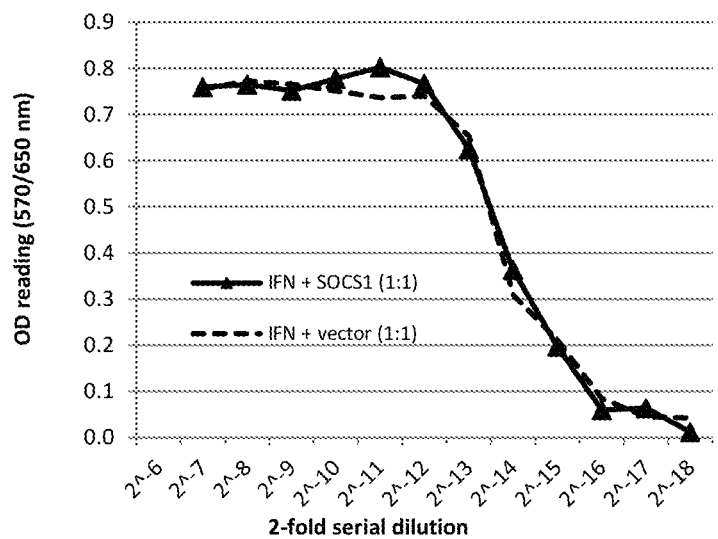
FIG. 8A, FIG. 8B, FIG. 8C, FIG. 8D, FIG. 8E, and FIG. 8F show the OD readings of MTT-based CPER assay using LFBK-αvβ6 and supernatants harvested from LFBK-αvβ6 cells co-transfected with different ratios of plasmid DNA inserted with IFNα and SOCS1 or vector only; at days 2 (FIG. 8A, FIG. 8B), 4 (FIG. 8C, FIG. 8D) and 6 (FIG. 8E, FIG. 8F) post-transfection as described below.
Figure 8B:
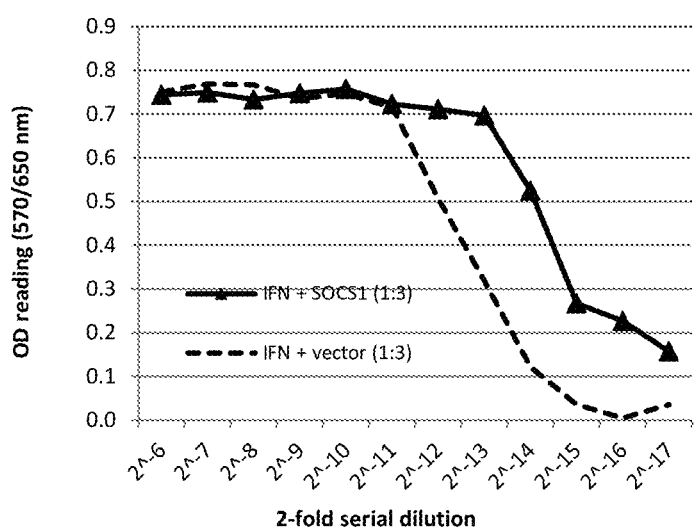
Figure 8C:
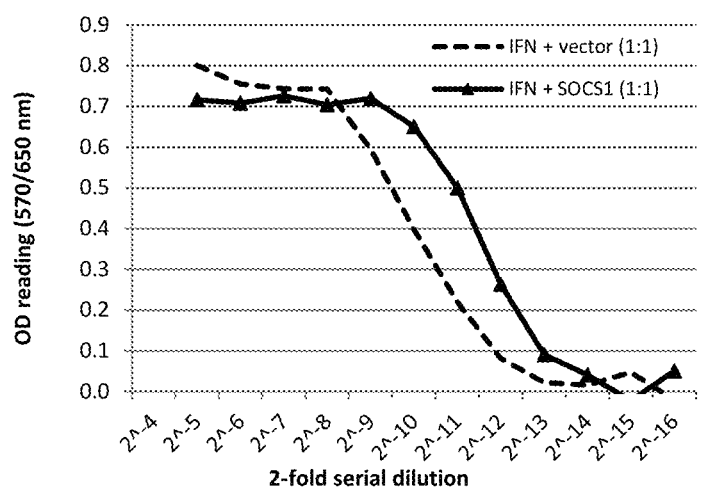
Figure 8D:
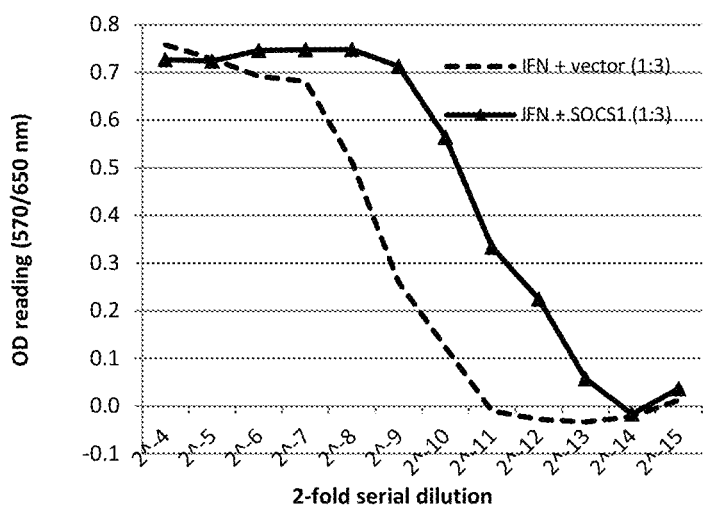
Figure 8E:
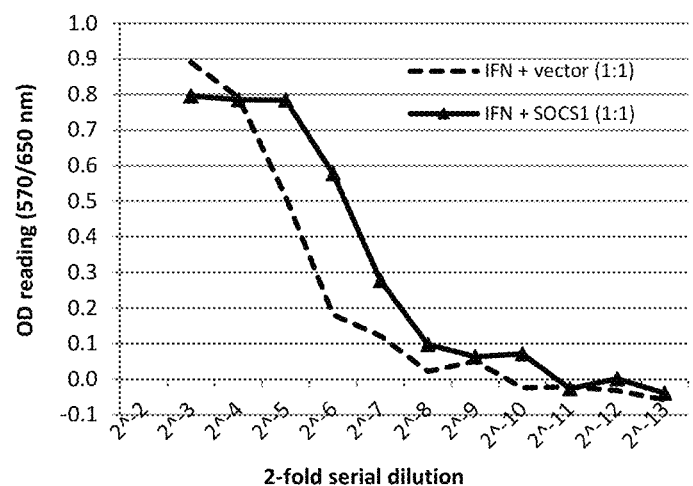
Figure 8F:
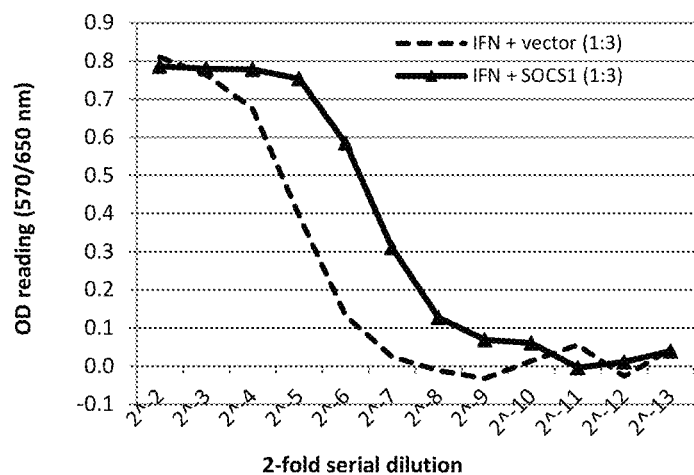
Figure 9A:
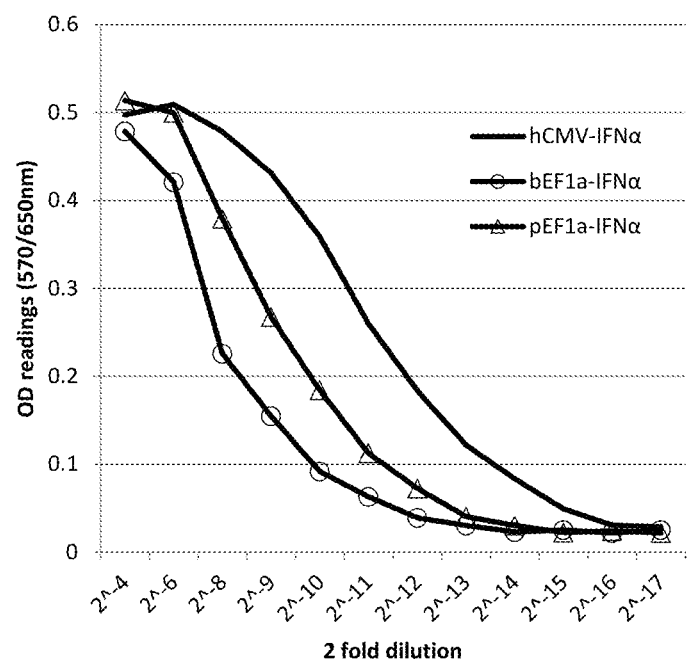
FIG. 9A and FIG. 9B show the OD readings of MTT-based CPER assay using LFBK-αvβ6 and supernatants harvested from HEK293 (FIG. 9A) and LFBK-αvβ6 (FIG. 9B) cells transfected with plasmid DNA containing an IFNα gene inserted at 3' end of CMV or EF1α promoters at day 1 post-transfection as described below.
Figure 9B:
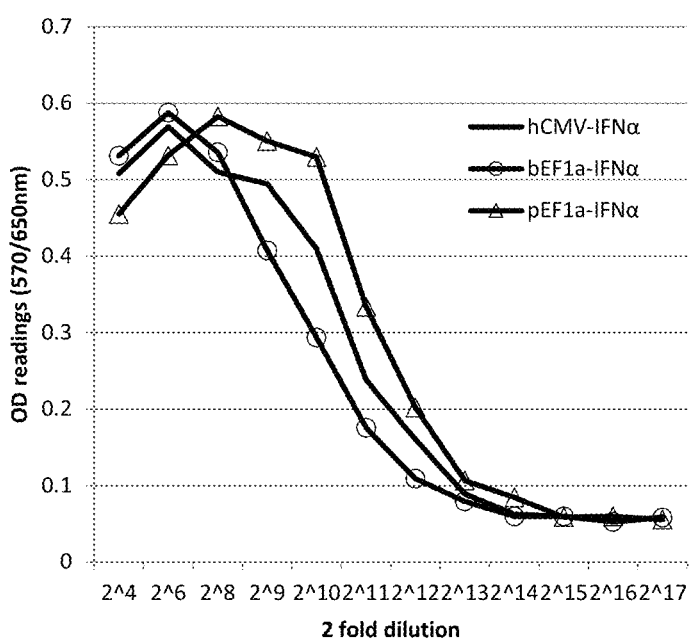
Figure 11A:
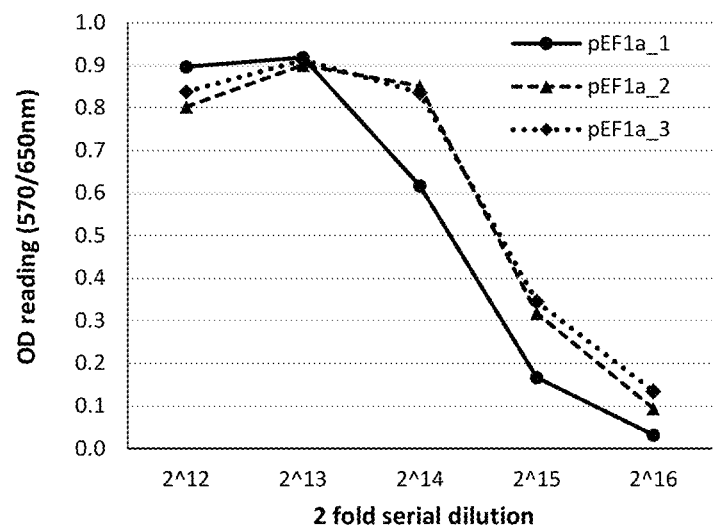
FIG. 11A and FIG. 11B show the OD readings of MTT-based CPER assay using LFBK-αvβ6 and supernatants harvested from LFBK-αvβ6 cells transfected with plasmid DNA containing three different porcine EF1α promoters inserted at 5' end of IFN19 coding sequence; at days 1 (FIG. 11A) and 2 (FIG. 11B) post-transfection as described below.
Figure 11B:
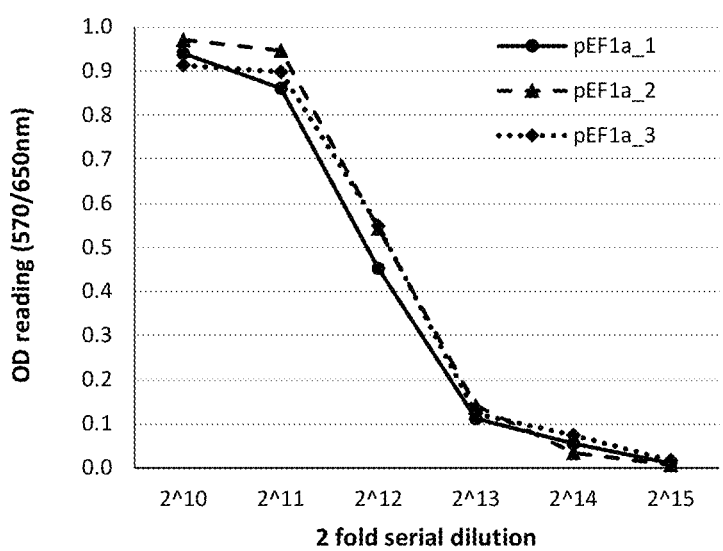
Figure 12A:
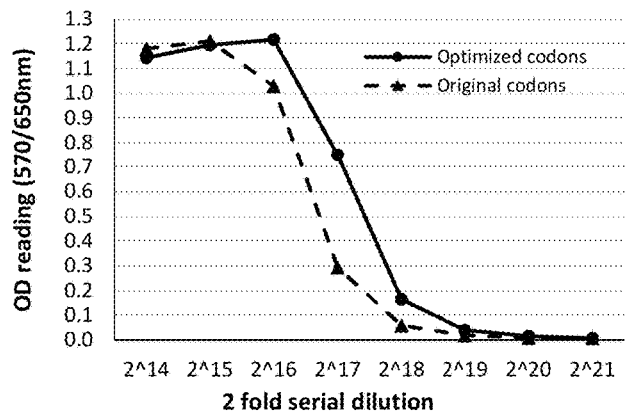
FIG. 12A, FIG. 12B, and FIG. 12C show the OD readings of MTT-based CPER assay using LFBK-αvβ6 and supernatants harvested from LFBK-αvβ6 cells transfected with plasmid DNA containing an NCS-IFN19+polyA termination sequence+porcine EF1α promoter+SOCS1 or codon-optimized SOCS1+polyA termination sequence+porcine EF1α promoter+optimized NCS-IFN19 at day 2 post-transfection; at days 1 (FIG. 12A), 2 (FIG. 12B) and 3 (FIG. 12C) post transfection as described below.
Figure 12B:
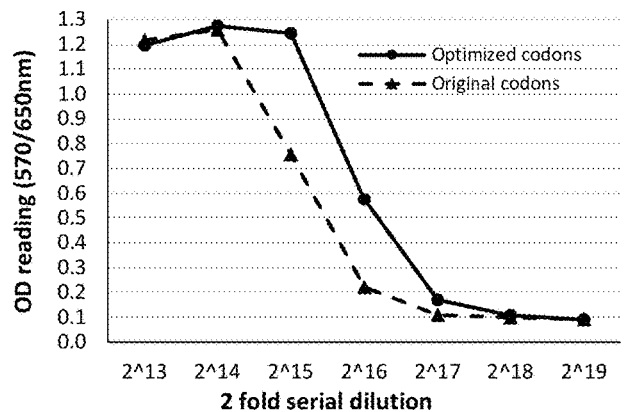
Figure 12C:
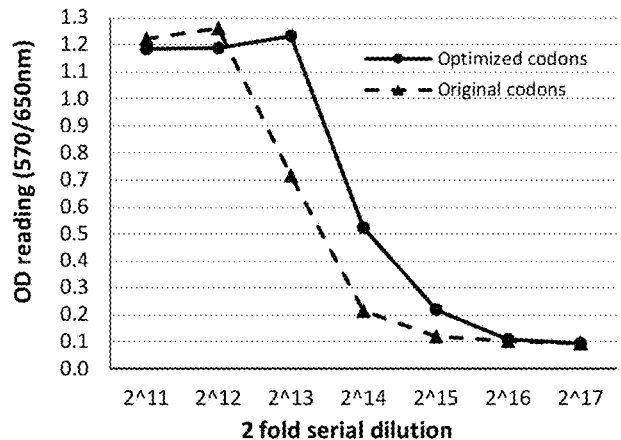
Figure 13A:
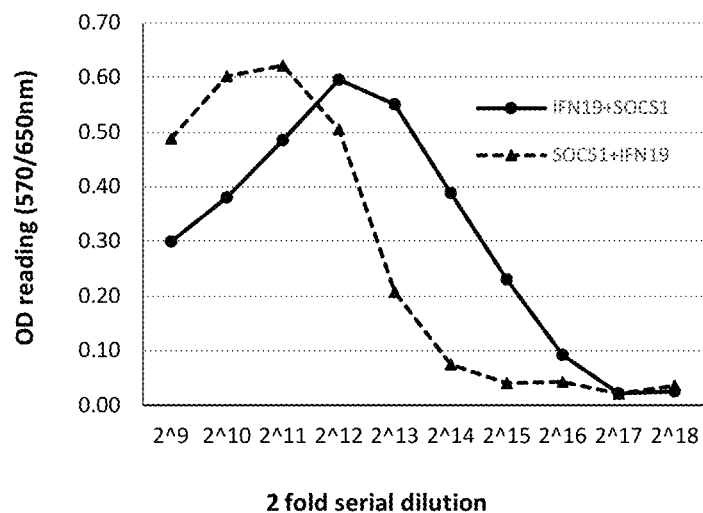
FIG. 13A and FIG. 13B show the OD readings of MTT-based CPER assay using LFBK-αvβ6 and supernatants harvested from LFBK-αvβ6 cells transfected with plasmid DNA containing an NCS-IFN19+polyA termination sequence+porcine EF1α promoter+SOCS1 or SOCS1+polyA termination sequence+porcine EF1α promoter+NCS-IFN19; at days 2 (FIG. 13A) and 3 (FIG. 13B) post-transfection as described below.
Figure 13B:
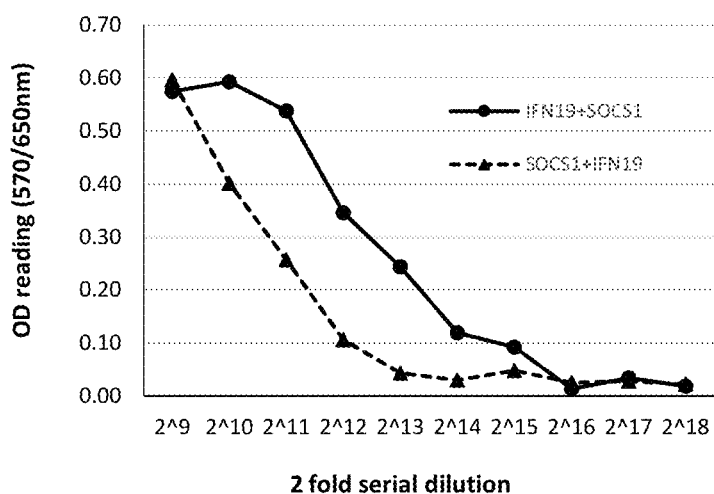
Figure 14:
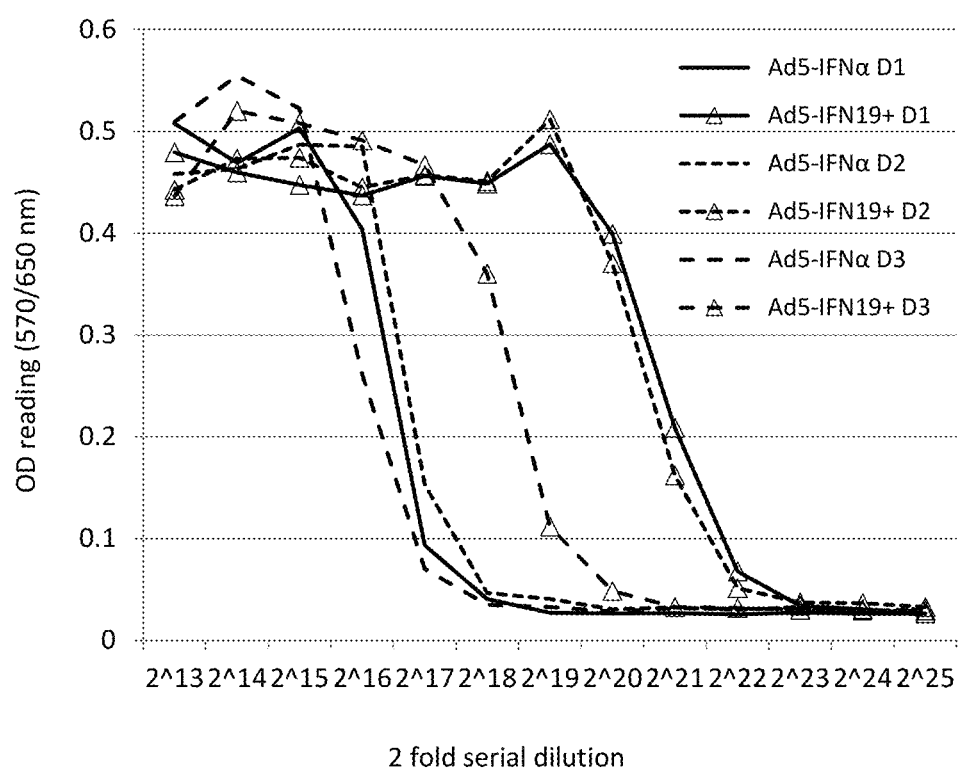
FIG. 14 shows the OD readings of MTT-CPER assays using IBRS-2 and supernatants harvested from LFBK-αvβ6 cells infected with 46 MOI of Ad5-IFN19+ or Ad5-IFNα virus at Days (D) 1, 2 and 3 post infection as described below.
Figure 15:
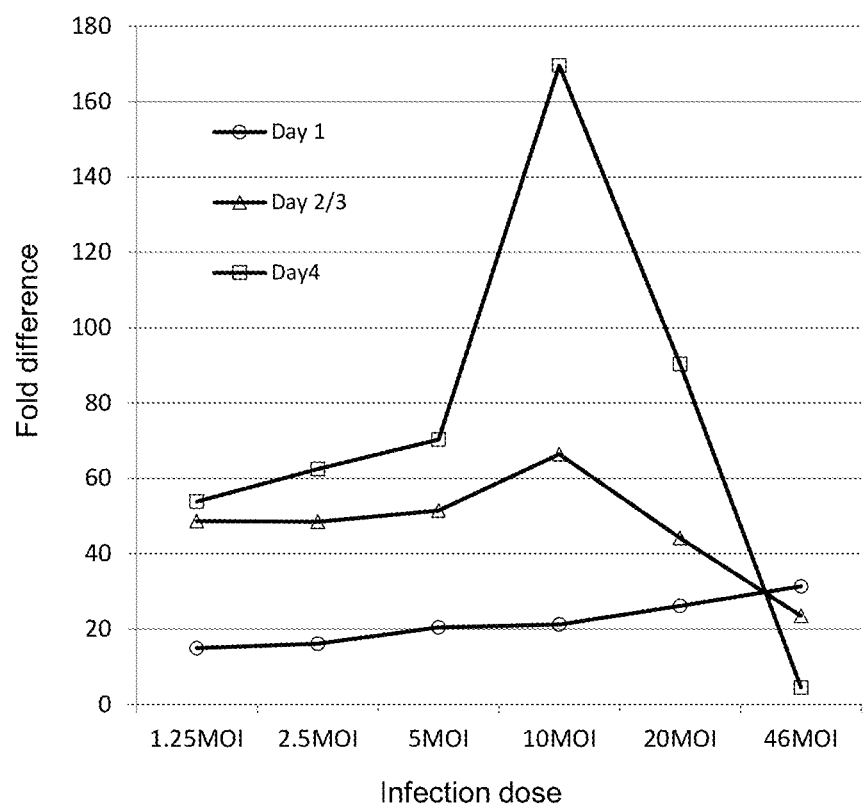
FIG. 15 shows the differences in anti-FMDV activities between Ad5-IFN19+ and Ad5-IFNα at days 1, 2-3 and 4 post infection of different MOI as described below.
Figure 16A:
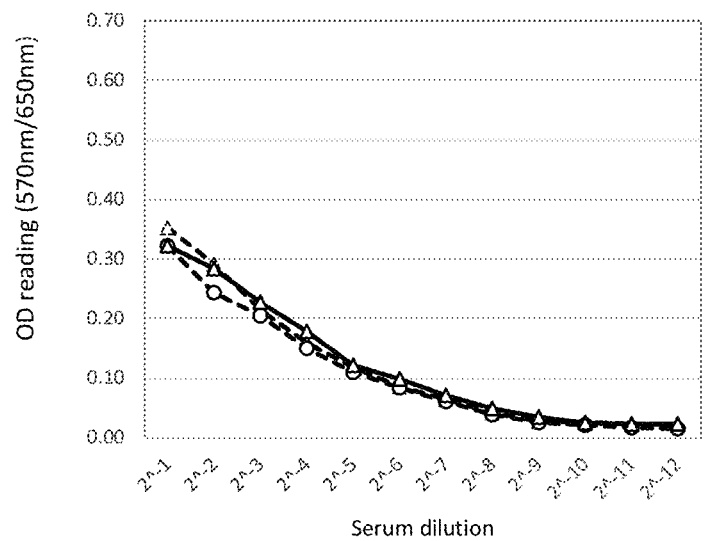
FIG. 16A, FIG. 16B, FIG. 16C, FIG. 16D, FIG. 16E, FIG. 16F, FIG. 16G, and FIG. 16H show anti-FMDV activities (OD readings) in sera of pig treated with Ad5-IFNα (dash lines) and Ad5-IFN19+ (solid line) at a dose of $10^9$ PFU (triangle) or $10^{10}$ PFU (circle) one day before treatment (FIG. 16A) and days 1, 2, 3, 4, 5, 6, and 7 post-treatment (FIG. 16B, FIG. 16C, FIG. 16D, FIG. 16E, FIG. 16F, FIG. 16G, and FIG. 16H, respectively) as described below.
Figure 16B:
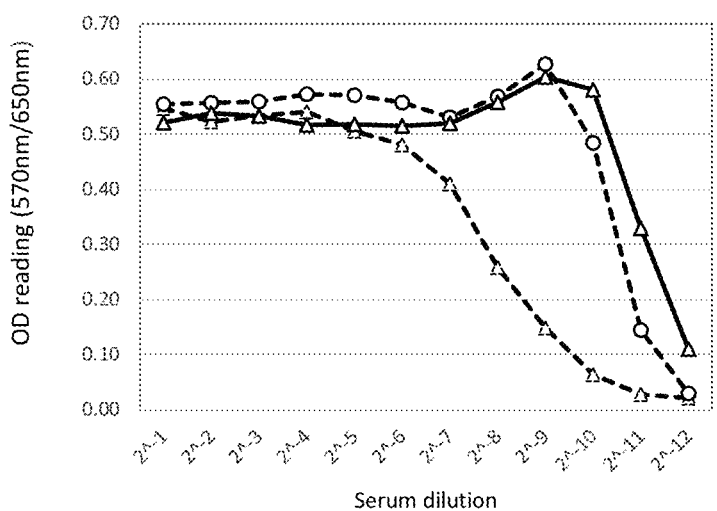
Figure 16C:
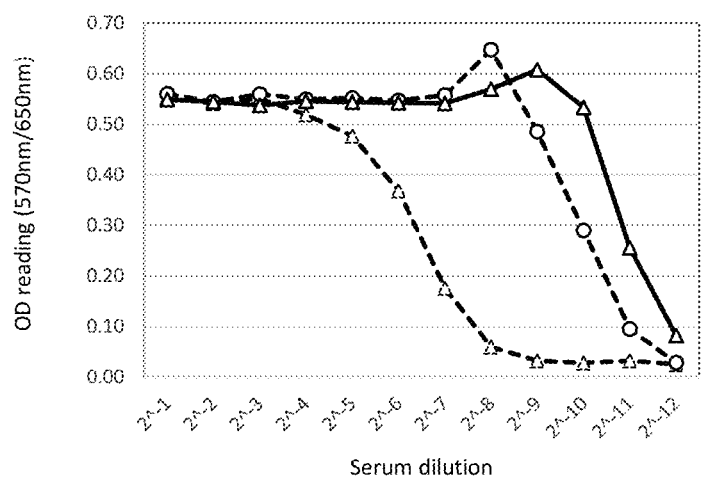
Figure 16D:
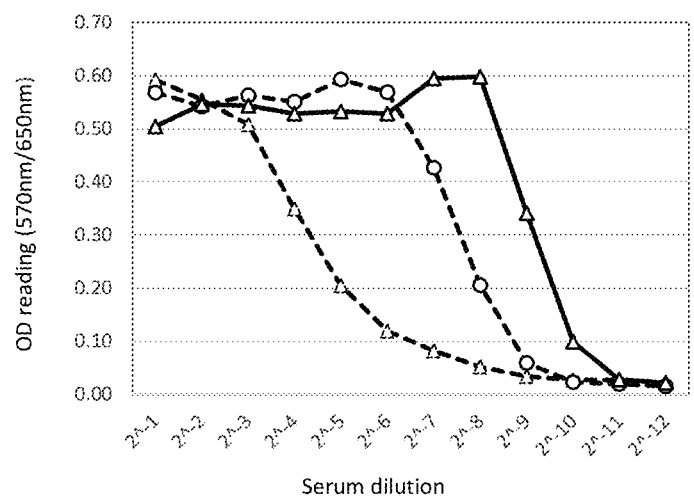
Figure 16E:
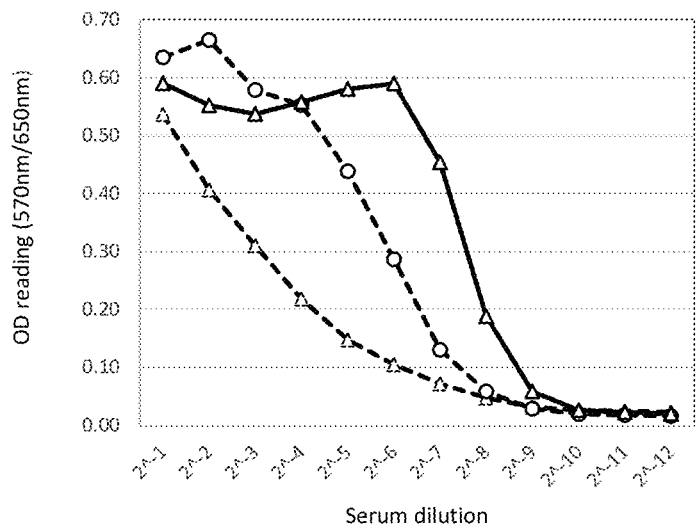
Figure 16F:
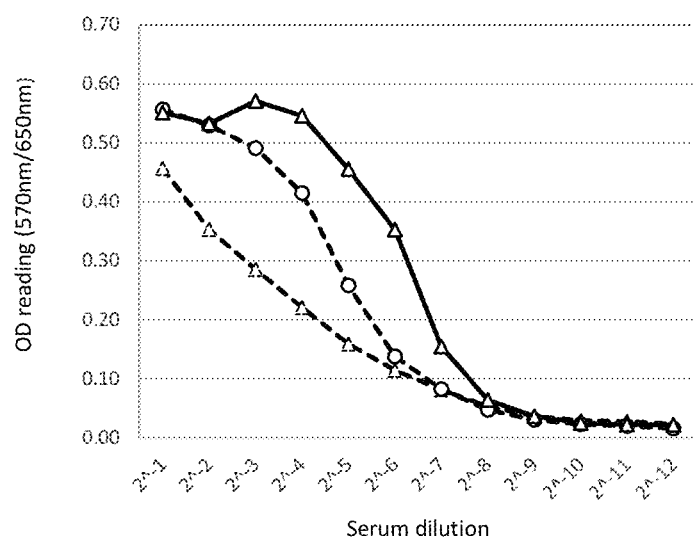
Figure 16G:
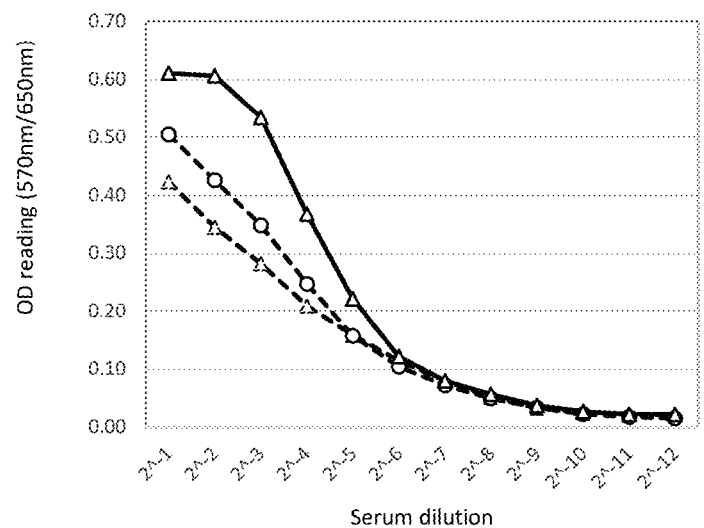
Figure 16H:
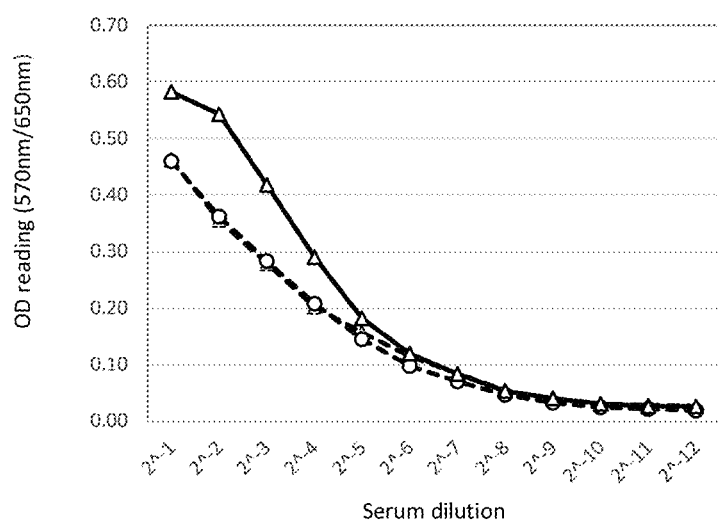
Figure 17:
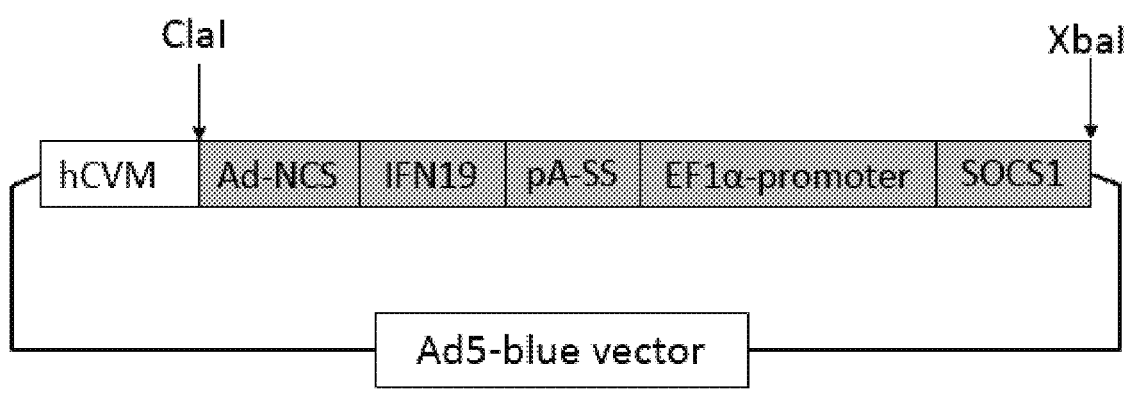
FIG. 17 shows the structure of the Ad5-blue plasmid used to produce Ad5-IFN19+recombinant adenovirus where hCMV (human cytomegalovirus promoter), Ad-NCS (adenovirus tripartite non-coding sequence), IFN19 (the porcine IFNα coding sequence of GQ415066), pA-SS (the poly-A signal sequence of bovine growth hormone), EF1α-promoter (the promoter of porcine EF1α gene), and SOCS1 (the porcine SOCS1 coding sequence) were concatenated and inserted between ClaI and Xba restriction sites of the Ad5-blue vector.

There are two transcription start sites in bovine and porcine EF1α promoters associated with two TATA box like sequences (1st TATATAA and 2nd TTTAAAG). The first TATA box is more resemble to the consensus sequence than the second one. To increase the transcription activity of porcine EF1α promoter, pEF1α_1, we constructed two new promoters, (1) pEF1α_2 with mutated 2nd TATA box (from TTTAAAG to TATAAAT) and (2) pEF1α_3 with additional 70 nucleotide deletion in the first intron of pEF1α_2 as shown in FIG. 1. These promoters were cloned into pcDNA3.1 plasmid for DNA transfection and the test of the induced antiviral activity as described earlier.

Codon frequency can affect the translation efficiency of mRNA. Transcription activity of CMV and pEF1α promoter is different in different cells. Differences in the expression levels between IFN19 and SOCS1 may affect the magnitude of antiviral activity induced from the cells transfected with these genes. To test the effects of codon frequency and gene locations, we synthesized three DNA fragments containing (1) NCS-IFN19+polyA termination sequence+porcine EF1α promoter+SOCS1 as shown in FIG. 2, (2) the fragment 1 with codon-optimized IFN19 and SOCS1 provided by Genescript, and (3) the fragment 1 with location swap between SOCS1 and NCS-IFN19. These three fragments were inserted into pcDNA3.1 vector to test effects of codon optimization and gene swap on anti-FMDV activity induced from DNA transfected cells as described earlier.

Adenovirus production: Ad5 Blue plasmid vector (Moraes, M. P., et al., Biotechniques, 31: 1050 (November 2001)) was used to produce recombinant adenoviruses expressing the genes of interest. A porcine IFNα gene previously tested in pigs (Chinsangaram et al., 2003) and the IFN with the highest anti-FMDV activity identified in our study (IFN19) were cloned into the vector between ClaI and XbaI restriction sites. The plasmids with the correct inserts were purified with Qiagen plasmid miniprep kits (Qiagen) and used to transfect HEK293 cells with Lipofectamine in Opti-MEM after linearization with PacI restriction enzyme (New England Biolabs, Ipswich, Mass.). The recombinant viruses were isolated from the plaques, propagated in HEK293 cells, and purified with CsCl gradient centrifugation. These two recombinant adenoviruses were named as Ad5_IFNα (previously tested) and Ad5-IFN19 (Ad5 with the best IFN gene). To construct recombinant adenovirus containing IFN19 and SOCS1 coding sequences, a poly-A termination sequence, the promoter of porcine EF1α gene, and the coding sequence of porcine SOCS1 were inserted at the 3'-end of the coding sequence of the best IFN gene (FIG. 15). This DNA fragment was inserted into the Ad5-blue vector to produce the recombinant adenovirus as described earlier. The recombinant virus produced from the plasmid was named as Ad5-IFN19+SOCS1 or Ad5-IFN19+.

Adenovirus titration: Titers of recombinant adenoviruses were determined based on tissue culture infectious dose (TCID50) using HEK293 cell monolayer in 96 well plates according to Moraes et al. (Moraes, M. P., et al., Vaccine, 20(11-12): 1631-1639 (2002)). Briefly, the cells were plated at a density of $1\times10^4$ cells per well, incubated at 37° C. with 5% $CO_2$ for 3 days or 95-100% confluency. Tenfold serial dilutions starting at $10^{-5}$ to $10^{-12}$ in Minimum Essential Medium (MEM, GIBCO) were prepared in 1.7 ml sterile micro-centrifuge tubes. Prior to inoculation, the cell culture media was removed and 100 μl per well of the diluted samples was added. Sixteen replicates per dilution and eight dilutions per titration with two independent replications were performed. The plates were incubated at 37° C., 5% $CO_2$ and checked for the presence of CPE (cytopathic effect) daily for 10 days. Spearman-Karber 50% endpoint viral titers were calculated for TCID50.

Antiviral activity induced by adenoviruses: To measure the anti-FMDV activity of the recombinant adenoviruses, LFBK-αvβ6 cells cultured in 24-well plates were infected at different MOIs of recombinant adenoviruses (2-fold serial dilution with the serum-free medium) for 1 hour. After the infection, the viruses were removed and the wells were washed three times with medium. Fresh growth medium was added to each well and cell culture supernatants were collected at different time points after the infection and filtered using Centricon® 30 filters (Millipore, Billerica, Mass.). The anti-FMDV activity of the supernatants was measured with the MTT-CPER assay as described earlier.

Animal testing: Commercial pigs (body weight at 50-60 LB) were injected subcutaneously with one of three recombinant adenoviruses (the existing adenovirus: Ad5-IFNα and Ad5IFN19+) at $10^{10}$ (FMD protective dose) and/or $10^9$ plaque forming unit (PFU) per pig. There were four pigs per treatment group including a control group injected with PBS only. The available amount of Ad5-IFN19+ was enough only for three pigs at $10^9$ PFU per animal. Blood samples (5 ml) were collected at one day before injection and at days 1, 2, 3, 4, 5, 6 and 7 post injection. Sera were prepared from the blood samples for measuring anti-FMDV activity using MTT-CPER assay as described earlier. 2-fold serial dilutions of serum samples ($2^1$ to $2^{12}$) were used in the assay. Three replications per sample were conducted in the MTT-CPER assay. The animal use protocol was reviewed and approved by Animal Use Review Committees at the University of Nebraska and the in-vivo experiment was conducted in the animal facility located at the College of Veterinary Medicine, University of Nebraska. The serum samples were shipped to Plum Island Animal Disease Center on dry ice for MTT-CPER assays.

Results. Example 1. Expression of porcine IFNα and β genes: All porcine IFNα proteins were highly expressed in the cell line using Lipofectamine mediated transient DNA transfection with significant variations in expression levels based on Western blotting results (FIG. 1). All IFN tested displayed two bands (one with and another without glycosylation) as expected. DNA transfection with pcDNA3.1-vector alone also induced low IFN expression on the Western blot (Lane 8 in FIG. 1). FIG. 1 shows very similar intensity of the protein bands on the Western blot for the supernatants harvested from the transfections of equal amount of DNA plasmids inserted with different IFNα genes. The results indicated that the transient IFN expression is a reliable approach to produce IFN proteins for comparing the antiviral activity of the IFN genes.

Anti-FMDV activity of porcine IFNα and β genes: The supernatants harvested from the transfections of DNA plasmid without IFN gene displayed very low anti-FMDV activity in the MTT-CPER assays (data not shown). To test the reproducibility of plasmid transfection and the MTT-CPER assay, supernatants harvested from two transfections using two independent plasmids with identical coding sequences displayed nearly identical OD readings in the MTT-CPER assay (data not shown), indicating the approach was accurate regarding assessing the antiviral activity of specific porcine IFN genes.

Among 32 porcine IFN a genes tested, surprisingly Gene GQ415066 (named IFN19 in this study) consistently displayed the highest anti-FMDV activity in the MTT-CPER assays using two cell lines (IBRS-2 and LFBK-αvβ6) and cell culture supernatants harvested at two different time points (2 and 4 days post-DNA transfection) (Table 1, FIG. 2, FIG. 4, and FIG. 5). Table 1 shows the anti-FMDV EC50 of in-vitro expressed porcine interferons α and β calculated from the OD readings of MTT-based CPER assays as described below. Table 1 lists the normalized EC50 of tested IFN genes with indexes of anti-FMDV activity relative to the best gene. The activity at days 2 and 4 were highly correlated ($r^2$=0.95 among IFNα). The supernatants from the DNA transfections of one IFN gene (AJKK01221111) from the miniature pig and three (GQ415061, NM_001164860, and XM_003121882) from the commercial pigs surprisingly could not fully protect the cells against FMDV infection at the 16-fold dilutions (the highest tested concentration of the supernatants in this study). Based on the calculated EC50, the differences in anti-FMDV activity between the best IFNα gene and others tested ranged from approximately 2- to more than 1,000-fold.

Five reported porcine IFNβ genes also showed substantial differences in anti-FMDV activity with a high correlation between days 2 and 4 ($r^2$=0.99). The antiviral activity of the best IFNβ gene (AY687281) was approximately 6-fold lower than that of the best IFNα, whereas the activity of JF906509 was not detectable in this study (Table 1 and FIG. 2). Interestingly, the decreases in anti-FMDV activity from day 2 to 4 were much greater for IFNβ (averaging ~200 fold) than those for IFNα (averaging ~30 folds), indicating porcine IFNβ may not be good gene source for biotherapeutics.

Anti-FMDV activity of adenovirus containing IFN19: A recombinant Ad5 virus containing GQ415066 or IFN19 gene (Ad5-IFN19) was produced and validated by DNA sequencing. The Ad5 virus (Ad5-IFNα) inserted with an IFNα gene previously tested in pigs (Chinsangaram et al., 2003; Dias et al., 2011; Moraes et al., 2003) was also produced to serve as a benchmark control. These Ad5 viruses were titrated twice and used to infect LFBK-αvβ6 cells at different MOI (six 2-fold serial dilutions starting at MOI of 46). The anti-FMDV activities of the supernatants from Ad5-IFNα and Ad5-IFN19 infections decreased linearly with the dilution factors (data not shown). No CPE was observed in the cells infected with these two viruses at the MOI tested. At the same MOI, the EC50 values for the Ad5-IFN19 virus surprisingly were approximately four-fold higher than those of Ad5-IFNα (only two MOI shown in FIG. 6), which suggested that the anti-FMDV activity of the recombinant adenovirus containing the best porcine IFN gene was surprisingly about four time higher than that of the adenovirus previously tested.

In summary, we identified the best porcine IFN gene from 37 porcine IFNα and β genes. A new recombinant adenovirus inserted with this gene surprisingly was approximately 4-fold more potent to the one tested previously in pigs. Therefore, using this new adenovirus can improve the potency of the IFN biotherapeutics in pigs.

Discussion: Adenovirus-based IFN biotherapeutics is very effective in completely protecting pigs against FMDV infection (Chinsangaram et al., 2003; Dias et al., 2011; Moraes et al., 2003); however, this approach requires a protective dose approximately 100 times higher than adenovirus-based vaccines. Reducing the protective dose is critical for making the biotherapeutics feasible. One objective of this study was to identify the most potent IFN genes for use in the biotherapeutics. To identify the best IFN gene, we applied an approach similar to the method used by Zanotti et al. (Zanotti et al., 2015) to produce IFN for antiviral activity assays using a colorimetric MTT assay we previously developed (Ramanathan et al., 2015). Our results from two identical plasmids yielded nearly identical results, indicating these assays are highly reproducible.

The differences in the antiviral activity of porcine type I interferons have been tested against PRRSV and VSV infection in different cell lines (Sang et al., 2010; Zanotti et al., 2015). There were substantial differences among the genes tested. In the study by Sang et al. (Sang et al., 2010), porcine IFNα6 (GQ415060) was the top interferon against PRRSV and VSV in MARC-15 cells, whereas IFNα12 (GQ415066 or IFN19 in our study) was the best interferon against VSV in PK-15 cells. Similarly, in the study by Zanotti et al. (Zanotti et al., 2015), IFNα6 was the interferon with the highest anti-VSV activity and IFNα12 was the second best; however, it is unknown if the coding sequence of the IFNα12 is identical to GQ415066. IFN19 has also been demonstrated to be the most potent interferon against CSFV (classical swine fever virus) in swine macrophages (Fernandez-Sainz, I., et al., Virology, 483: 284-290 (2015)). Our results indicated that IFN19 or IFNα12 was the best anti-FMDV interferon.

One interesting result we found was that the antiviral activity provided by IFβ genes decreased surprisingly more rapidly than that by IFNα genes. It has been reported that IFNβ displays a higher anti-proliferation activity in some cell types (Rosenblum, M. G., et al., J. Interferon Res., 10: 141-151 (1990)), and tyk2-deficient cells retain partial responsiveness to IFN-β but are completely unresponsive to IFN-αs (John, J., et al., Mol. Cell Biol., 11: 4189-4195 (1991)), which, without being bound by theory, may explain the rapid decrease in its antiviral activity after treatment. It appears that porcine IFNβ may not be a good candidate for antiviral biotherapeutics due to its lower and short lasting antiviral effect compared to IFNα.

After identification of the best porcine IFN gene, we inserted it into the same Ad5-blue vector to produce a recombinant adenovirus to compare with the adenovirus previously tested in pigs. These in-vitro results surprisingly showed that this new adenovirus was approximately four-fold more potent in terms of inducing antiviral activity after infection than the one previously tested. We subsequently used other approaches in combination with this best IFN gene to further improve the potency in order to make the biotherapeutics feasible.

Example 2. Effect of non-coding sequence (NCS) on IFN production: FIG. 7A, FIG. 7B, and FIG. 7C show that the transfection of the plasmid inserted with IFNα containing the adenovirus tripartite NCS surprisingly induced higher (approximately 2 fold) antiviral activity than that of plasmid inserted with IFNα without the NCS in the supernatants harvested at days 2, 4 and 6 post transfection. In contrast, surprisingly there were no differences between the supernatants from transfections with plasmids inserted with IFNα containing 3' end NCS of ACTA (data not shown). Based on these results, two recombinant adenoviruses were produced from the Ad5 virus inserted with the IFNα genes with and without the NCS (NCS-IFNα and IFNα, respectively). NCS-IFNα surprisingly induced approximately 2-fold higher antiviral activity than Ad5-IFNα did in the supernatants harvested at days 2, 4 and 6 from the cells infected at MOI of 20 (only day 6 shown in FIG. 7D). Therefore, both in-vitro tests using plasmids and adenoviruses showed that the adenovirus tripartite NCS surprisingly enhanced the expression of the recombinant IFN from the Ad5 virus.

Effect of SOCS1 on IFN production: Co-transfection of pcDNA3.1-IFNα and pcDNA3.1-SOCS1 at 1:1 ratio surprisingly increased the antiviral activity of the supernatants harvested on days 4 and 6 but not on day 2 when it was compared to the co-transfection of pcDNA3.1-IFNα and pcDNA3.1 vector only at the same ratio (FIG. 8A, FIG. 8C, FIG. 8E). Interestingly, when the ratios (IFNα: SOCS1) were increased to 1:3, the increases in anti-FMDV activity were observed on days 2, 4 and 6, indicating positive dose effect of SOCS1 on the antiviral activity (FIG. 8B, FIG. 8D, FIG. 8F). These results indicated that SOCS1 genes delivered together with an IFNα gene surprisingly increased the interferon expression.

Transcription activity of EF1α promoters: The transfection of pcDNA3.1-hCMV-IFNα produced the highest anti-FMDV activity among transfections of the three plasmids in HEK293 (FIG. 9A); however, the anti-FMDV activity of the supernatants from the transfection of the pcDNA3.1-pEF1α-IFNα was highest among the transfections in LFBK-αvβ6 cells (FIG. 9B). These results indicated that the promoter activity was species specific. Surprisingly, the transcription activity of porcine EF1α promoter was higher than the hCMV promoter in porcine cells. Mutation of second TATA box slightly increased (less than 2-fold) the induced anti-FMDV activity of the supernatants from cell culture transfected with the plasmid DNA at day 1 post DNA transfection, while the deletion of additional 70 nucleotide did not have the effect on the activity (FIG. 11). The differences became much smaller at day 2 post transfection. Without being bound by theory, these results suggested that changing the second TATA box like sequence to the censuses sequence increased the transcription activity of the promoter and the intron might have little effect on transcription.

Effect of codon optimization of IFN19 and SOCS1: FIG. 12 shows that transfection of plasmid DNA containing codon-optimized IFN19 and SOCS1 open reading frames surprisingly induced higher the anti-FMDV activity by approximately 2-fold than that of non-optimized sequences. The differences between optimized and non-optimized sequence were greater at day 2 than those at day 1, while the differences remain the same at day 3 post transfection. These results indicated that codon optimization increased transcription activity of the open reading frames.

Effect of position swap between IFN19 and SOCS1: FIG. 13 showed that there was an effect of promoter and gene pairing on the antiviral activity induced with DNA transfection. Plasmids constructed using pCMV-NCS-IFN19 and pEF1α-S0051 produced higher antiviral activity by more than 2-fold that those with pCMV-SOCS1 and pEF1α-NCS-IFN19 at days 1, 2 and 3 post-transfection (only day 2 and 3 shown in FIG. 12). Together with other results presented earlier, these results suggested that the expression level of SOCS1 surprisingly plays a more important role in inducing anti-FMDV activity than that of IFN19.

Anti-FMDV activity of adenovirus containing NCS-IFN19 and EF1α-SOCS1: A recombinant adenovirus inserted with IFN19 containing the adenovirus tripartite NCS (NCS-IFN19) and the SOCS1 gene with porcine EF1α promoter (EF1α-SOCS1) was produced and named as Ad5-IFN19+ (FIG. 17). To compare Ad5-IFN19+ with Ad5-IFNα, we infected LFBK-αvβ6 cells with the viruses at MOI of 46. Unlike Ad5-IFNα and Ad5-IFN19 infections, Ad5-IFN19+ infection induced CPE in the cells after infection at MOI of 46. FIG. 4 shows the antiviral activities induced by Ad5-IFN19+ infection at days 1, and 2 post-infection surprisingly was approximately 16 times (24 fold) higher than those by Ad5-IFNα infection, whereas the differences at day 3 post infection were much smaller (~4 time), presumably, without being bound by theory, due to CPE. These results surprisingly demonstrated that SOCS1 significantly enhanced IFN expression.

To reduce CPE of Ad5-IFN19+ on LFBK-αvβ6, we infected the cells with 2-fold serially diluted Ad5-IFN19+ staring at MOI of 20. Ad5-IFN19+ virus infection caused CPE at MOI of 10 and 20 with a dose effect. To assess the differences in the antiviral activity between Ad5-IFNα and Ad5-IFN19+, we calculated EC50 for the antiviral activity of all supernatants harvested from different MOIs of infection. The differences in MOI and OD readings were also taken into account for the antiviral activity. FIG. 5 shows that Ad5-IFN19+ virus infection surprisingly produced approximately 16-30-fold higher antiviral activity in day 1 post-infection than Ad5-IFNα. The fold differences surprisingly increased at days 2/3 and 4 ranging from approximately 50- to 170-fold except for MOIs of 20 and 46. The differences in anti-FMDV activity decreased when MOI was greater than 10. The differences in antiviral activity among infection doses suggested that the effect of SOCS1 and the cytotoxicity were correlated with induced anti-FMDV activity.

Anti-FMDV activity of Ad5-IFN19+ in pigs: Before the injection of recombinant adenoviruses, the sera in all pigs showed very similar background anti-FMDV activities (FIG. 6A). All background activities could not fully protect the tested cells from FMDV infection at the highest tested serum concentration (2-fold dilution) based on the OD readings of the positive controls (wells without FMDV, OD readings at 0.60). The anti-FMDV activity in the sera of the group injected with PBS remained practically the same throughout the entire test period (data not shown). One pig injected with Ad5-IFNα and all with Ad5-IFN19+ showed jaundice. All pigs injected with Ad5-IFN19+ also displayed other symptoms of sickness and one had to be euthanized at day 2 post injection. The pigs with jaundice in the Ad5-IFNα group had the highest anti-FMDV activity in its group, likewise the antiviral activity of the euthanized pig was the highest in its group. The results show that jaundice and sickness after injection were highly correlated with anti-FMDV activity in the sera.

Anti-FMDV activity induced by Ad5-IFNα displayed a positive dose effect equivalent to the difference between the doses. The antiviral activity at day 1 post injection was the highest and then decreased by at least two-fold each day (FIG. 6). The anti-viral activity fell below the full protection level at day 4 post injection with $10^9$ PFU (FIG. 6E) and at day 6 with $10^{10}$ PFU (FIG. 6G). There was a difference of more than four-fold in antiviral activity between individuals with the highest and the lowest anti-FMDV activity in this group.

Surprisingly, the pigs injected with Ad5-IFN19+ displayed the highest anti-FMDV activity among the groups at all days post injection with no decrease at day 2 (FIG. 6B and FIG. 6C). Then the antiviral activity gradually decreased but surprisingly remained at very close to the full protection level at day 7 post injection (FIG. 6H). It appears that the differences between the groups injected with Ad5-IFN19+ and Ad5-IFNα started at day 1 post injection and the differences increased up to day 4 and then decreased afterward, indicating antiviral effect induced by Ad5-IFN19+ not only was surprisingly greater but also surprisingly lasted longer if taking both the dose and the activity into consideration.

In summary, based on these in-vitro and in-vivo results, we have improved the potency of an existing IFN biotherapeutics using four elements: (1) the IFN gene with the highest anti-FMDV activity (i.e., IFN19), (2) the adenovirus tripartite sequence, (3) the EF1α promoter, and (4) the SOCS1 gene. The improvement included surprisingly increased in both the magnitude and duration of induced anti-FMDV activity as showed in the in-vitro and in-vivo results though the differences between Ad5-IFNα and Ad-IFN19+ in-vivo were smaller than those in-vitro. Taking both dose and antiviral activity into consideration, we have surprisingly improved the IFN biotherapeutics by more than 20-fold compared to the one tested previously.

Discussion: Adenovirus-based IFN biotherapeutics are very effective in completely protecting pigs against FMDV infection (Chinsangaram et al. 2003; Dias et al. 2011; Moraes et al. 2003); however, this approach requires a protective dose approximately 100 times higher than adenovirus-based vaccines. Reducing the protective dose is critical for making the biotherapeutics feasible. We have successfully applied several approaches to enhance the potency of the biotherapeutics. In our study described above, we identified the most potent IFN genes and used that gene to replace the one in the adenovirus previously tested in pigs. However, this approach improved the potency of the biotherapeutics surprisingly by only 4-fold. We then applied other approaches (use of the four elements described above) via enhancing IFN production to surprisingly improve the potency further.

The first approach was to increase the production of IFN by enhancing IFN mRNA stability and translation efficiency. Non-coding sequences (NCS) have been known to regulate mRNA stability and translation efficiency (Barrett, L. W., et al., Cell Mol. Life Sci., 69 (21): 3613-3634 (2012)). We did not observe any effects of 3' end NCS of ACTA1 on IFN production, but found positive effect of the adenovirus tripartite sequence on the expression of the recombinant protein in our in-vitro testing. Without being bound by theory, the IFN production was increased probably via a mechanism associated with translation efficiency.

The second approach was to reduce the negative impacts of intrinsic effects of the expressed recombinant protein IFN. We constructed a porcine EF1α promoter that showed a higher transcription activity than the human CMV promoter in the porcine cells. Using this promoter, we inserted another gene, SOCS1, into the adenovirus to reduce the effects from IFN signaling on IFN producing cells. This recombinant adenovirus surprisingly induced an in-vitro anti-FMDV activity up to 170-fold higher than the existing Ad5-IFNα virus. We observed very similar patterns of SOCS1 effect on induced antiviral activity in in-vitro and in-vivo tests, although much smaller differences were observed in pigs than those in cell culture. The differences probably were due, without being bound by theory, to hundreds-fold higher IFN concentrations induced in cell culture than those in animals, which provided an environment for SOCS1 to play a bigger role in-vitro than in-vivo. Without being bound by theory, the effect of SOCS1 could be explained by reducing both apoptotic effect of IFN on IFN-producing cells and inhibitory effect of IFN on protein translation. Slower decreases of anti-FMDV activity induced by Ad5-IFN19+ both in-vitro and in-vivo than those by Ad5-IFNα also support the explanations.

Taking the differences in injection doses, serum antiviral activities, and the euthanized pig (having the highest antiviral activity in its group) into consideration, we estimate that this new biotherapeutics has a potency surprisingly more than 20 times higher than the one tested previously. Other clinical observations also supported the increase of potency. Jaundice has been observed as a side-effect associated with high IFN concentrations in pigs (Chinsangaram et al. 2003; Dias et al. 2011; Moraes et al. 2003). Even at ten-fold lower than the reported protective dose, all pigs injected with Ad5-IFN19+ surprisingly showed more severe jaundice and other symptoms of sickness than other pigs in this study. In this study, these symptoms were positively correlated with the anti-FMDV activity in the sera. The Ad5-IFN19+ also showed higher cytotoxicity in our in-vitro studies than the Ad5-IFNα.

In summary, we have significantly improved the potency of the existing IFN biotherapeutics for pigs surprisingly by greater than 20-fold using four biological elements. Based on the scale of the enhancement, without being bound by theory, these four elements appeared to act synergistically. This new biotherapeutics can induce higher and longer anti-FMDV activity than the one previously tested in pigs.

All of the references cited herein, including U.S. Patents and U.S. Patent Application Publications, are incorporated by reference in their entirety. Also incorporated by reference in their entirety are the following references: Castaldello, A., et al., J. Cell Physiol., 224: 702-709 (2010); Chawla-Sarkar, M., et al., Apoptosis, 8 (3): 237-49 (2003).

Thus, in view of the above, there is described (in part) the following:

A recombinant adenovirus genome, said adenovirus genome comprising (or consisting essentially of or consisting of) a heterologous nucleic acid inserted into a cloning site of said genome, said heterologous nucleic acid comprising (or consisting essentially of or consisting of):

a. a first nucleic acid sequence comprising (or consisting essentially of or consisting of) an adenovirus tripartite sequence operably linked to a second nucleic acid sequence encoding an interferon;

b. a third nucleic acid sequence comprising (or consisting essentially of or consisting of) a bovine growth hormone polyA termination sequence operably linked to said second nucleic acid sequence;

c. a fourth nucleic acid sequence comprising (or consisting essentially of or consisting of) a porcine elongation factor 1-alpha (EF1α) promoter;

d. a fifth nucleic acid sequence operably linked to said fourth nucleic acid sequence, said fifth nucleic acid sequence encoding a suppressor of cytokine signaling 1 (SOCS1) protein.

The above adenovirus genome, wherein the second nucleic acid sequence is codon-optimized for a bacterial host cell. The adenovirus genome, wherein the bacterial host is *E. coli*.

The above adenovirus genome, wherein the fifth nucleic acid sequence is codon-optimized for a bacterial host cell. The adenovirus genome, wherein the bacterial host is *E. coli*.

The above adenovirus genome, wherein said fourth and fifth nucleic acid sequences are positioned 3' to said third nucleic acid sequence.

The above adenovirus genome, wherein said heterologous nucleic acid comprises SEQ ID NO:6.

The above adenovirus genome, wherein said first nucleic acid sequence comprises SEQ ID NO:1, wherein said second nucleic acid sequence comprises SEQ ID NO:2, wherein said third nucleic acid sequence comprises SEQ ID NO:3, wherein said fourth nucleic acid sequence comprises SEQ ID NO:4, and wherein said fifth nucleic acid sequence comprises SEQ ID NO:5.

The above adenovirus genome, wherein said adenovirus genome further comprises vector sequences, said vector sequences allowing for replication of an adenovirus in a host cell. The adenovirus genome, wherein said host cell is a bacterial cell. The adenovirus genome, wherein said bacterial cell is an *E. coli* cell.

A host cell comprising (or consisting essentially of or consisting of) the above adenovirus genome.

A recombinant virus produced by the above recombinant adenovirus genome.

A method of producing interferon in an animal comprising (or consisting essentially of or consisting of) introducing into said animal (e.g., swine) an effective amount of the above recombinant virus. The method, wherein said introducing is by intramuscular, subcutaneous, oral or intranasal inoculation. The method said method comprising introducing into said animal an effective amount of the virus and a veterinary or pharmaceutically acceptable carrier.

A method of producing interferon in tissue culture comprising (or consisting essentially of or consisting of) growing a cell comprising the above adenovirus genome under in vitro conditions allowing for the production of interferon, thereby producing interferon. The method, wherein the cell is a bacterial cell.

An immunomodulatory composition comprising (or consisting essentially of or consisting of) the above recombinant virus and a veterinary or pharmaceutically acceptable carrier.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

The EC50 of porcine interferons α and β genes expressed from IBRS-2 cells transfected with pcDNA3.1 inserted with interferon genes

| Gene | Type | Day 2 EC50 | Day 2 Index | Day 4 EC50 | Day 4 Index |
| --- | --- | --- | --- | --- | --- |
| GQ415066 | α | 537025 | 1.000 | 21901 | 1.000 |
| AOCR01001737 | α | 329558 | 0.614 | 12083 | 0.552 |
| AJKK01220487 | α | 307724 | 0.573 | 7711 | 0.352 |
| GQ415060 | α | 296130 | 0.551 | 9772 | 0.446 |
| AJKK01153977 | α | 200159 | 0.373 | 5059 | 0.231 |
| XM_003480504 | α | 143237 | 0.267 | 9696 | 0.443 |
| AOCR01194172 | α | 101432 | 0.189 | 2670 | 0.122 |
| GQ415056 | α | 97004 | 0.181 | 3814 | 0.174 |
| NM_0011995375 | α | 96768 | 0.180 | 4049 | 0.185 |
| AJKK01148380 | α | 83962 | 0.156 | 1568 | 0.072 |
| AJKK01240321 | α | 83327 | 0.155 | 3194 | 0.146 |
| AJKK01153980 | α | 80698 | 0.150 | 4180 | 0.191 |
| XM_003480505 | α | 76442 | 0.142 | 4762 | 0.217 |
| AOCR01194178 | α | 74862 | 0.139 | 1421 | 0.065 |
| DQ872659 | α | 67009 | 0.125 | 2988 | 0.136 |
| AOCR01194172-2 | α | 61482 | 0.114 | 1220 | 0.056 |
| NM_001166319 | α | 53063 | 0.099 | 2464 | 0.113 |
| XM_003480507 | α | 45761 | 0.085 | 2787 | 0.127 |
| XM_005660067 | α | 45205 | 0.084 | 2747 | 0.125 |
| AOCR01027891 | α | 43572 | 0.081 | 1337 | 0.061 |
| NM_001195377 | α | 31527 | 0.059 | 1490 | 0.068 |
| XM_003353504 | α | 18092 | 0.034 | 574 | 0.026 |
| NM_001164855 | α | 17022 | 0.032 | 836 | 0.038 |
| NM_001166311 | α | 16282 | 0.030 | 666 | 0.030 |
| XM_003480495 | α | 7586 | 0.014 | 468 | 0.021 |
| AJKK01266018 | α | 7015 | 0.013 | 235 | 0.011 |
| X57191 | α | 3219 | 0.006 | 313 | 0.014 |
| XM_003353507 | α | 905 | 0.002 | 69 | 0.003 |
| GQ415061 | α | ND* | | ND | |
| NM_001164860 | α | ND | | ND | |
| XM_003121882 | α | ND | | ND | |
| AJKK01221111 | α | ND | | ND | |
| AY687281 | β | 83637 | 0.156 | 514 | 0.023 |
| GQ415073 | β | 29304 | 0.055 | 143 | 0.007 |
| KF414741 | β | 7336 | 0.014 | 57 | 0.003 |
| EF104599 | β | 357 | 0.001 | ND | |
| JF906509 | β | ND | | ND | |

ND: EC50 could not be reliably estimated with the MTT-CPER assay due to low anti-FMDV activity.

We claim:

1. A recombinant adenoviral vector, whose genome comprises:
   a. a nucleic acid sequence encoding interferon (IFN); and
   b. a nucleic acid sequence encoding a suppressor of cytokine signaling 1 (SOCS1) operably linked to a porcine elongation factor 1-alpha (EF1α) promoter.

2. The recombinant adenoviral vector of claim 1, wherein the nucleic acid sequence encoding IFN is codon-optimized for expression in bacteria.

3. The recombinant adenoviral vector of claim 2, wherein the bacteria is *E. coli*.

4. The recombinant adenoviral vector of claim 1, wherein the nucleic acid sequence encoding a SOCS1 protein is codon optimized for expression in bacteria.

5. The recombinant adenoviral vector of claim 4, wherein the bacteria is *E. coli*.

6. The recombinant adenoviral vector of claim 1, wherein the nucleic acid sequence encoding a SOCS1 protein operably linked to the porcine EF1α promoter is 3' to the nucleic acid sequence encoding IFN.

7. The recombinant adenoviral vector of claim 1, wherein the genome of the adenovirus comprises the nucleic acid sequence of SEQ ID NO:6.

8. The recombinant adenoviral vector of claim 1, wherein the nucleic acid sequence encoding IFN comprises the nucleic acid sequence of SEQ ID NO: 2, the nucleic acid sequence encoding the EF1α promoter comprises the nucleic acid sequence of SEQ ID NO: 4, and the SOCS1 comprises the nucleic acid sequence of SEQ ID NO: 5.

9. The recombinant adenoviral vector of claim 1, further comprising vector sequences allowing for replication of an adenovirus in a host cell.

10. The recombinant adenoviral vector of claim 9, wherein said host cell is a bacteria.

11. The recombinant adenoviral vector of claim 10, wherein the bacteria is *E. coli*.

12. An isolated host cell comprising the adenoviral vector according to claim 1.

13. A method of producing IFN in a swine, the method comprising introducing the adenovirus of claim 1 into the swine such that IFN is produced in the swine.

14. The method of claim 13, wherein said introducing is by muscular, subcutaneous, oral or intranasal inoculation.

15. The method of claim 13, wherein the adenovirus is introduced in a veterinary or pharmaceutically acceptable carrier.

16. A method of producing IFN in tissue culture, the method comprising: introducing the adenovirus of claim 1 into cells in culture such that the IFN is produced.

17. The method of claim 16, wherein the cell is a bacterial cell.

18. An immunomodulatory composition comprising the adenovirus of claim 1 in a veterinary or pharmaceutically acceptable carrier.

19. The recombinant adenoviral vector of claim 1, further comprising a bovine growth hormone polyA termination sequence operably linked to the nucleic acid sequence encoding IFN.

* * * * *